(12) United States Patent
Zhao et al.

(10) Patent No.: US 7,683,092 B2
(45) Date of Patent: Mar. 23, 2010

(54) CRYSTALLINE FORMS OF ANTIDIABETIC COMPOUNDS

(75) Inventors: Dalian Zhao, Fanwood, NJ (US);
Jean-Francois Marcoux, St-Symphorien d'Ozon (FR); David Boardman, Norristown, NJ (US); Aquiles E. Leyes, Schwenksville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 40 days.

(21) Appl. No.: 11/885,842

(22) PCT Filed: Mar. 10, 2006

(86) PCT No.: PCT/US2006/008476
§ 371 (c)(1), (2), (4) Date: Sep. 6, 2007

(87) PCT Pub. No.: WO2006/099077
PCT Pub. Date: Sep. 21, 2006

(65) Prior Publication Data
US 2008/0221198 A1   Sep. 11, 2008

Related U.S. Application Data

(60) Provisional application No. 60/660,476, filed on Mar. 10, 2005.

(51) Int. Cl.
A61K 31/404 (2006.01)
C07D 209/18 (2006.01)

(52) U.S. Cl. ...................... 514/419; 548/493
(58) Field of Classification Search .......... 514/419; 548/493
See application file for complete search history.

(56) References Cited

U.S. PATENT DOCUMENTS

| | | | |
|---|---|---|---|
| 5,956,431 | A | 9/1999 | Iourcha et al. |
| 6,452,602 | B1 | 9/2002 | Morein |
| 6,593,925 | B1 | 7/2003 | Hakura et al. |
| 6,658,146 | B1 | 12/2003 | Iourcha et al. |
| 6,683,978 | B1 | 1/2004 | Iourcha et al. |
| 6,775,417 | B2 | 8/2004 | Hong et al. |
| 6,819,793 | B1 | 11/2004 | Reshetov et al. |
| 7,186,746 | B2 * | 3/2007 | Acton et al. ............ 514/419 |
| 2003/0138152 | A1 | 7/2003 | Fenny |

FOREIGN PATENT DOCUMENTS

| | | |
|---|---|---|
| EP | 1 400 929 | 3/2004 |
| EP | 1 445 734 | 8/2004 |
| WO | WO 2004/020408 | 3/2004 |
| WO | WO 2004/020409 | 3/2004 |

OTHER PUBLICATIONS

Vippagunta et al., Crystallline solids, at p. 4, Advanced Drug Delivery Reviews, vol. 48, (2001), pp. 3-26.*
Office Action with Combined Search and Examination report dated Oct. 24, 2007, in corresponding United Kingdom Application No. GB0718106.8.
Office Action with Combined Search and Examination Report dated Oct. 25, 2007, in corresponding United Kingdom Application No. GB0718110.0.
International Search Report and Written Opinion for International Application No. PCT/GB2006/000769 dated Sep. 19, 2006.
Dudgeon et al, "Algorithms for Graphics Texture Mapping," System Theory, 1991, Proceedings, Twenty-third Southeastern Symposium on Columbia, SC, USA Mar. 10-12, 1991, Los Alamitos, CA, USA; IEEE Comput. Soc., US, Mar. 10, 1991, pp. 613-617, XP010024578.
Ivanof et al, "Color Distribution—A New Approach to Texture Compression", Computer Graphics Forum, Amsterdam, N1, vol. 19, No. 3, Aug. 21, 2000, pp. C283-C289, C535, XP009008909.
Drost et al., "A Hybrid System for Real-Time Lossless Image Compression", Microprocessors and Microsystems, IPC Business Press Ltd., London, GB, vol. 25, No. 1, Mar. 15, 2001, pp. 19-31, XP004317581.
Ljosland, "3D and Video in a Single Core", Electronics World, Sep. 2005, vol. 111, No. 1833, Sep. 2005, pp. 34-37, XP008068631.
Chen et al., "A JPEG-Like Texture Compression with Adaptive Quantization for 3D Graphics Application", Visual Computer Springer-Verlag Germany, vol. 18, No. 1, Feb. 2002, pp. 29-40, XP001149442.
Fenney, "Texture Compression Using Low-Frequency Signal Modulation", Graphics Hardware, Jul. 2003.
Ström et al., Packman—Texture Compression for Mobile Phones, Ericsson Research, SIGGRAPH2004.

* cited by examiner

*Primary Examiner*—Yong Chu
(74) *Attorney, Agent, or Firm*—Richard C. Billups; Catherine D. Fitch

(57) ABSTRACT

Novel crystalline forms of two indole compounds connected to phenoxyalkylcarboxylic acid groups are selective PPAR gamma partial agonists that are useful in the treatment of type 2 diabetes, hyperglycemia, obesity, dyslipidemia, and the metabolic syndrome. The novel crystal forms include a crystalline free acid dihydrate and crystalline free acid anhydrate of one compound and several crystalline forms of the free acid and the sodium salt of the second compound. The invention also relates to pharmaceutical compositions comprising these novel crystal forms, processes to prepare the crystal forms and their pharmaceutical compositions, and uses of the crystal forms in the treatment of type 2 diabetes and other PPAR gamma modulated diseases.

4 Claims, 20 Drawing Sheets

US 7,683,092 B2

CRYSTALLINE FORMS OF ANTIDIABETIC COMPOUNDS

CROSS-REFERENCE TO RELATED APPLICATIONS

This application is a U.S. National Phase application under 35 U.S.C. §371 of PCT Application No. PCT/US2006/008476, filed Mar. 10, 2006, which claims priority under 35 U.S.C. §119 from U.S. provisional application No. 60/660,476, filed Mar. 10, 2005.

FIELD OF THE INVENTION

The present invention relates to novel crystalline forms and salt forms of compounds that are useful as pharmaceutically active ingredients for the treatment of type 2 diabetes and other diseases that are modulated by PPAR gamma agonists, including hyperglycemia, obesity, dyslipidemia, and the metabolic condition. The compounds are selective PPAR gamma partial agonists (also known as a SPPARgM's or SPPARM's).

BACKGROUND OF THE INVENTION

Type 2 diabetes remains a serious medical problem. There is an ongoing need for new treatments that are more effective and that have fewer side effects.

SUMMARY OF THE INVENTION

The present invention is concerned with novel crystal forms, hydrates, anhydrates, and salts of compounds that belong to the class of compounds that are active as PPAR gamma partial agonists, also known as SPPARM's or SPPARgM's. Related compounds were originally disclosed published PCT application WO 2004/020409. Crystal forms, hydrates, anhydrates, and/or salts of two structurally similar compounds are disclosed: (1) The first compound is (2R)-2-{3-[3-(4-methoxybenzoyl)-2-methyl-6-(trifluoromethoxy)-1H-indol-1-yl]phenoxy}butanoic acid (Compound I), which is disclosed herein as a crystalline dihydrate and a crystalline anhydrate. The crystalline dihydrate and crystalline anhydrate forms disclosed herein have advantages over the previously disclosed amorphous form of (2R)-2-{3-[3-(4-methoxybenzoyl)-2-methyl-6-(trifluoromethoxy)-1H-indol-1-yl]phenoxy}butanoic acid, having properties that are advantageous in the preparation of pharmaceutical compositions, such as ease of purification, ease of processing, and stability of compositions. (2) The second compound is (2R)-2-{3-[[3-(4-chlorobenzoyl)-2-methyl-6-(trifluoromethoxy)-1H-indol-1-yl]methyl]phenoxy}butyric acid (Compound II), which is disclosed herein as a sodium salt having at least 5 novel crystalline polymorphic forms and a free acid having at least 3 novel polymorphic forms. Some of these polymorphic forms have advantages over the previously disclosed solid form of Compound II, having properties that are advantageous in the preparation of pharmaceutical compositions, such as ease of purification, ease of processing, lower hygroscopicity, and stability of compositions.

The invention also concerns pharmaceutical compositions containing the novel crystalline polymorphs; processes for the preparation of these polymorphic forms and their pharmaceutical compositions; and methods for using them for the treatment of type 2 diabetes, hyperglycemia, obesity, dyslipidemia, and the metabolic condition.

DETAILED DESCRIPTION OF THE INVENTION

Figure 1:
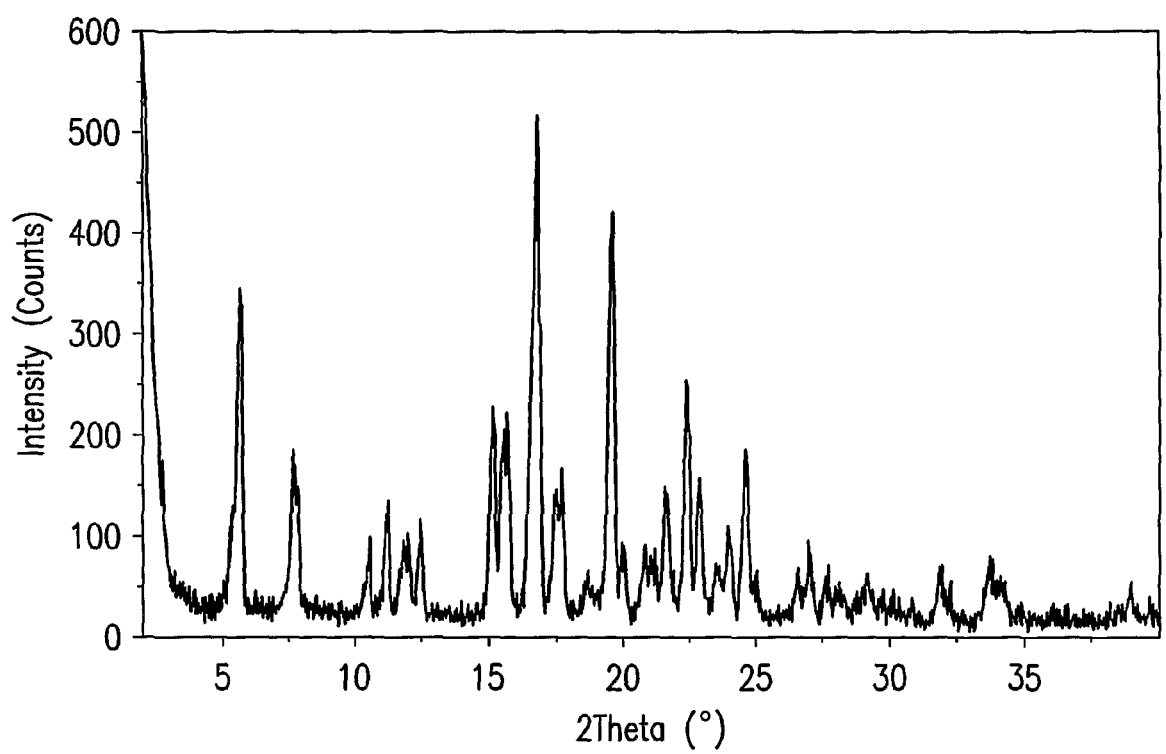
FIG. 1 provides a characteristic X-ray powder diffraction pattern of Compound I crystalline dihydrate.

This invention provides novel crystalline dihydrate and anhydrate polymorphic forms of (2R)-2-{3-[3-(4-methoxybenzoyl)-2-methyl-6-(trifluoromethoxy)-1H-indol-1-yl]phenoxy}butanoic acid having structural formula I (Compound I):

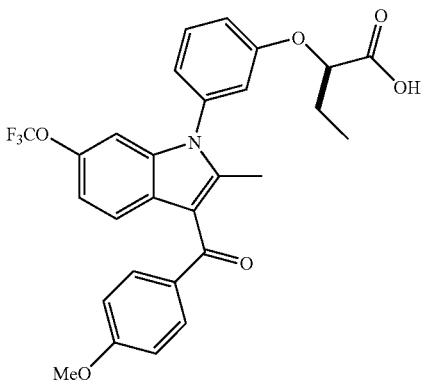

The structure above was first disclosed as Example 3 in the published PCT application W02004/020409. The compound isolated using the synthetic methodology in the '409 patent publication is an amorphous solid. The inventors herein have discovered a crystalline dihydrate and a crystalline anhydrate of the amorphous Compound I. These crystalline compounds are much more readily used in the preparation of pharmaceutical compositions. The crystalline dihydrate is readily converted to the crystalline anhydrate by warming it in a stream of dry nitrogen, and the crystalline anhydrate is readily converted back to the crystalline dihydrate by placing it in a stream of moist nitrogen (RH>70%). The crystalline dihydrate is non-hygroscopic.

A further embodiment of the present invention provides a drug substance that comprises the crystalline anhydrate or crystalline dihydrate form of Compound I in a detectable amount. By "drug substance" is meant the active pharmaceutical ingredient (API). The amount of crystalline anhydrate form or crystalline dihydrate form in the drug substance can be quantified by the use of physical methods such as X-ray powder diffraction (XRPD), solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy. In a class of this embodiment, about 5% to about 100% by weight of the crystalline anhydrate or crystalline dihydrate form is present in the drug substance. In a second class of this embodiment, about 10% to about 100% by weight of the crystalline anhydrate or crystalline dihydrate form is present in the drug substance. In a third class of this embodiment, about 25% to about 100% by weight of the crystalline anhydrate or crystalline dihydrate form is present in the drug substance. In a fourth class of this embodiment, about 50% to about 100% by weight of the crystalline anhydrate or crystalline dihydrate form is present in the drug substance. In a fifth class of this embodiment, about 75% to about 100% by weight of the crystalline anhydrate or crystalline dihydrate form is present in the drug substance. In a sixth class of this embodiment, substantially all of the Compound I drug substance is the crystalline anhydrate or crystalline dihydrate form, i.e., the Compound I drug substance is the substantially phase pure crystalline anhydrate or the phase pure crystalline dihydrate form.

Another aspect of the present invention provides a method for the treatment or control of clinical conditions for which a PPAR gamma agonist is indicated, which method comprises administering to a patient in need of such treatment or control a therapeutically effective amount of the crystalline anhydrate or crystalline dihydrate of Compound I or a pharmaceutical composition containing a therapeutically effective amount of the crystalline anhydrate or crystalline dihydrate form of Compound I. Such clinical conditions include Type 2 diabetes, hyperglycemia, obesity, dyslipidemia, and metabolic syndrome. A "patient" is a mammal, including a human. A patient is most often a human patient.

The present invention also provides for the use of the crystalline anhydrate or crystalline dihydrate form of the present invention in the manufacture of a medicament for the treatment or control in a patient of one or more clinical conditions for which a PPARgamma agonist is indicated. In one embodiment, the clinical condition is Type 2 diabetes.

Another aspect of the present invention provides the crystalline anhydrate or crystalline dihydrate form for use in the treatment or control in a patient of one or more clinical conditions for which a PPAR gamma agonist is indicated. In one embodiment of this aspect the clinical condition is Type 2 diabetes.

The present invention also provides pharmaceutical compositions comprising the crystalline anhydrate or crystalline dihydrate form, in association with one or more pharmaceutically acceptable carriers or excipients. In one embodiment the pharmaceutical composition comprises the active pharmaceutical ingredient (API) in admixture with pharmaceutically acceptable excipients wherein the API comprises a detectable amount of the crystalline anhydrate form or crystalline dihydrate form of the present invention. In a second embodiment the pharmaceutical composition comprises the API in admixture with pharmaceutically acceptable excipients wherein the API comprises about 5% to about 100% by weight of the crystalline anhydrate or crystalline dihydrate form of the present invention. In a class of this second embodiment, the API in such compositions comprises about 10% to about 100% by weight of the crystalline anhydrate or crystalline dihydrate form. In a second class of this embodiment, the API in such compositions comprises about 25% to about 100% by weight of the crystalline anhydrate or crystalline dihydrate form. In a third class of this embodiment, the API in such compositions comprises about 50% to about 100% by weight of the crystalline anhydrate or crystalline dihydrate form. In a fourth class of this embodiment, the API in such compositions comprises about 75% to about 100% by weight of the crystalline anhydrate or crystalline dihydrate form. In a fifth class of this embodiment, substantially all of the API is the crystalline anhydrate or crystalline dihydrate form of Compound I, i.e., the API is substantially phase pure Compound I in the crystalline anhydrate form or substantially phase pure Compound I in the crystalline dihydrate form.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17*th* ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition or to treat or control the condition.

Oral dosages of the present invention, when used for the indicated effects, will range between about 0.01 mg per kg of body weight per day (mg/kg/day) to about 100 mg/kg/day, and preferably 0.01 to 10 mg/kg/day. For oral administration, the compositions may be provided in the form of tablets or capsules containing for example 0.05, 0.1, 0.5, 1.0, 2.5, 5.0, 10.0, 15.0, 25.0, 50.0, 100, 200, 400, 600, 800, or 1000 milligrams of the API, measured in the form of the free acid, or such other doses that may be appropriate for the patient being treated to achieve a therapeutic result. A medicament typically contains from about 0.5 mg to about 500 mg of the API, preferably, from about 1 mg to about 200 mg of API. Intravenously, the most preferred doses will range from about 0.1 to about 10 mg/kg/minute during a constant rate infusion. Advantageously, the crystalline anhydrate and dihydrate forms of the present invention may be administered in a single daily dose, or the total daily dosage may be administered in divided doses of two, three or four times daily. Furthermore, the crystalline anhydrate and dihydrate forms of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the Compound I crystalline anhydrate form and crystalline dihydrate form herein described in detail can form the API, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral API can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include without limitation sodium oleate, sodium stearate, magnesium stearate, and sodium stearyl fumarate. Disintegrators include, without limitation, starch, methyl cellulose, agar, bentonite, xanthan gum and the like. Other commonly used additives that may be used include sodium benzoate, sodium acetate, sodium chloride and the like.

This invention likewise provides novel crystalline polymorphic forms of (2R)-2-{3-[[3-(4-chlorobenzoyl)-2-methyl-6-(trifluoromethoxy)-1H-indol-1-yl]methyl]phenoxy}butyric acid, having Formula II below and referred to herein as Compound II.

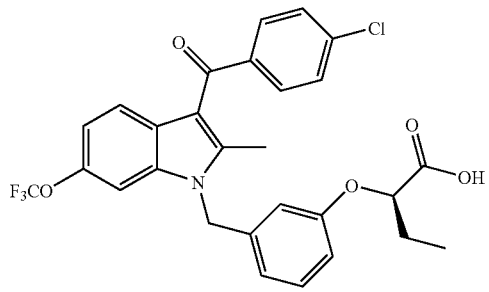

There are a wide range of crystal forms of Compound II with varying levels of stability and ease of preparation. Sodium salt Form V and free acid Form C are reproducibly prepared. Acid Form C is thermodynamically stable and is especially suitable for the preparation of pharmaceutical formulations. It is a non-hydrated crystalline compound.

These crystalline forms have embodiments that are analogous to those provided above for Compound I.

The following non-limiting Examples are intended to illustrate the present invention and should not be construed as being limitations on the scope or spirit of the instant invention.

Compounds I and II described herein may exist as tautomers such as keto-enol tautomers. The individual tautomers as well as mixtures thereof are encompassed within the compound of structural formula I.

EXAMPLE 1

Synthesis of (2R)-2-{3-[3-(4-methoxybenzoyl)-2-methyl-6-(trifluoromethoxy)-1H-indol-1-yl]phenoxy}butanoic acid (Compound I)

Compound I is made by the multi-step process shown below:

Step 1: Nitration

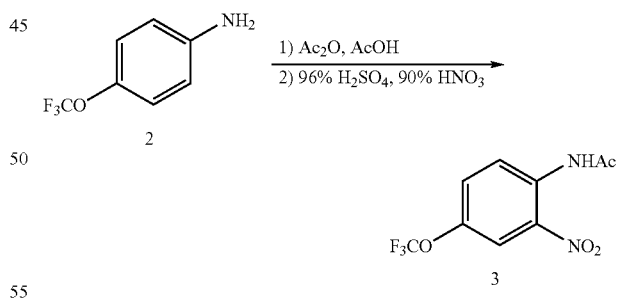

A vessel was charged with acetic acid (8.0 L) followed by 4-(trifluoromethoxy)aniline (8.00 Kg) via an addition funnel over 15-20 min with stirring at 20-35° C. Acetic anhydride (18.08 Kg) was then added at 20-35° C. over 15-20 min. The reaction mixture was stirred at 20-25° C. for 20-30 min. 96% Sulfuric acid (320 mL) was charged via an addition funnel over 5 min followed by 90% nitric acid (2.08 L) with stirring via another addition funnel over 60 min at 25-35° C. The reaction mixture was stirred at 20-25° C. for 0.5-1 h after the addition. Water (60 L) was added at 15-25° C. over 40-50 min with cooling. The solid product gradually crystallized after addition of 3-4 L water. The slurry was stirred at ambient temperature for 1 h and the yellow solid product isolated by filtration. The wet cake was washed with water (3×20 L) and dried using a nitrogen sweep to give dry product 3. Alternatively the quench described above can be carried out by pouring the reaction mixture into cold water.

Step 2: Hydrolysis

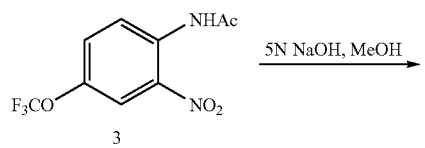

3

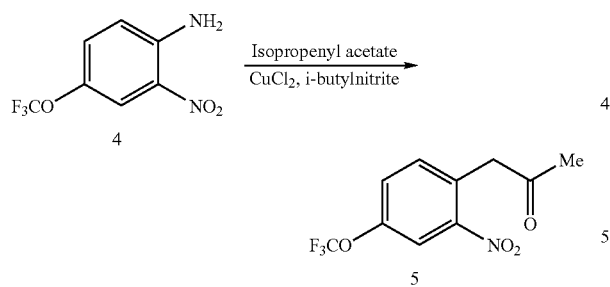

A vessel fitted with a mechanical stirrer, a thermometer probe, water cooling bath and an addition funnel was charged with 4-trifluoromethoxy-2-nitroacetanilide (11.0 Kg) and methanol (42 L) with stirring at ambient temperature. 5 N NaOH (10.41 L) was added to the slurry at 20-30° C. with water bath over 5-10 min to give a homogeneous dark amber solution. The reaction mixture was stirred at 25-30° C. for 1 h. After the reaction was complete, water (63 L) was added at 15-25° C. over 40-50 min with ice water bath. After addition of water, the batch was transferred to a 200 L vessel with mechanical stirring. The slurry was stirred at ambient temperature for another 2-3 h before filtration. The yellow solid product was isolated by filtration, and the wet cake was washed with 3:2 water/methanol (2×12.5 L) and dried under nitrogen with vacuum suction to give 2-nitro-4-trifluoromethoxyaniline 4.

Step 3: Meerwein Arylation

A vessel was charged with isopropenyl acetate (30 L) followed by copper(II)chloride (2.93 Kg) in one portion at 18-25° C. with stirring. The temperature of the solution was adjusted to 40-45° C. A solution of aniline 4 (4.05 Kg) in isopropenyl acetate (5 L) was added to the reaction mixture via an addition funnel over 1-2 h concomitantly with the addition of isobutyl nitrite (2.84 L) in a separate addition funnel over the same amount of time by keeping the reaction temperature at 40-50° C.

The reaction mixture was cooled to 18-22° C., diluted with toluene (21.5 L) and quenched by addition of 1.0 N HCl (21.5 L). The reaction mixture was stirred for 15 min. The organic layer was washed with water (21.5 L), NaHCO₃ aq sat (21.5 L) and water (2.5 L). The organic layer was concentrated under partial vacuum (max temp 20° C.) and the solvent switched to toluene. The volume was adjusted to 10.75 L and the homogeneous amber solution is cooled to 5 to −10° C. Heptane (3.6 L) was added and the mixture aged for 1 h. Heptane (37 L) was slowly added keeping the temperature at −5 to −10° C. The slurry was cooled to −25 to −20° C., aged 1 h at −25 to −20° C. and filtered. The dark yellow cake was washed with toluene/heptane (1:6 v/v, 11 L ) at −25 to −20° C., and heptane (4 L) at −25 to −20° C. and dried at ambient temperature under partial vacuum with a flow of nitrogen to afford the ketone 5.

Step 4: Indole

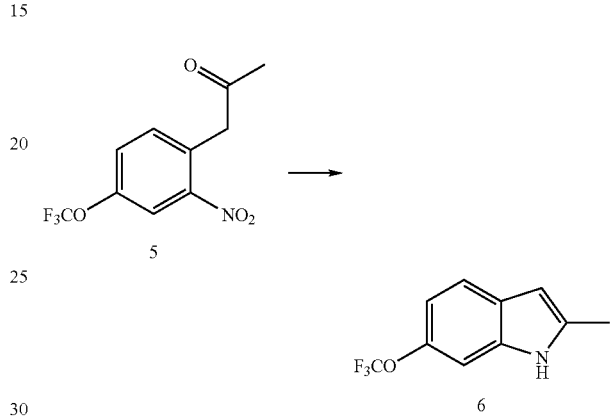

A slurry of the substrate 5 (2.0 Kg) and 5% Pd/C (484 g) in MeOH (7.6 L) was hydrogenated under an atmosphere of hydrogen at 15° C. for 1 to 2 h at 60 psi, and then heated to 65° C. for 6 h. The reaction mixture was filtered through solcafloc to remove the catalyst washing with MeOH. The batch was concentrated and solvent switched to toluene. The toluene solution of 6 was used as is in coupling step.

Step 5: 3-Benzyloxyiodobenzene

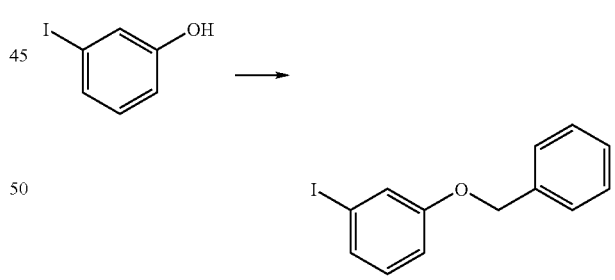

A vessel was charged with 3-iodophenol (6.8 Kg), powdered K₂CO₃ (5.12 Kg), DMF (40.8 L) and benzyl chloride (4.30 Kg). The resulting slurry was heated to 68-70° C. and stirred for 6-7 h. The reaction mixture was cooled to 35-40° C., and water (40.8 L) was added over 1 h with stirring at the same temperature. The resultant slurry was stirred at ambient temperature for 2-3 h after the water addition. The batch was filtered and the wet cake washed with water (3×35 L) and dried under nitrogen with a vacuum suction for 12-16 h giving product 7 as white crystalline solid.

Step 6: N-aryl Indole

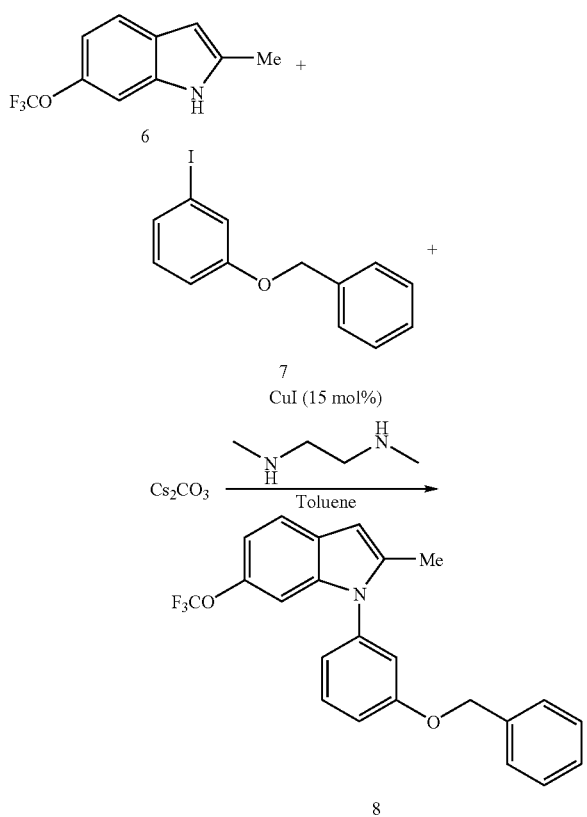

To a solution of indole 6 (3.20 Kg) in toluene (9.6 L) was added 3-benzyloxyiodobenzene 7 (4.57 Kg), CuI 421 g), N,N-dimethylethylene diamine 401 g) and cesium carbonate (9.4 Kg). Toluene (6.5 L) was added. The slurry was aged at 105-110° C. with vigorous stirring for 12 h and cooled to rt. Solka-floc (1.5 Kg) was added at 18-25° C., followed by toluene (30 L). Water (30 L) was then added dropwise over 30-60 min with good agitation. The mixture was aged for 1-2 hours at 18-25° and filtered. The cake was rinsed with toluene (10 L). The toluene filtrates were concentrated and the crude solution of 8 used directly in the next step. This reaction can also be advantageously carried out using $CuCl_2$ as catalyst at levels as low as 2 mol % with good mixing to keep the solids suspended (agitation or recycle loop from the bottom of the reactor) and using benzyloxyiodobenzene from the previous step that still has residual moisture. Exclusion of air is also advantageous.

Step 7: Acylation/Debenzylation

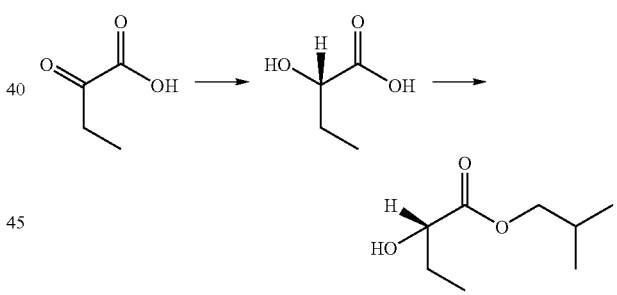

-continued

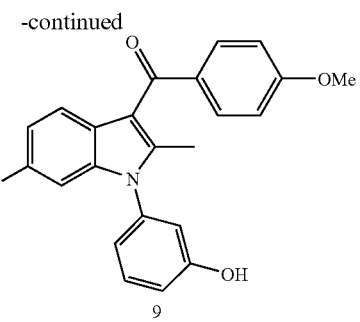

A solution of benzyloxyaryl indole 8 (2.58 Kg) in toluene (2.58 L) was cooled to 0° C. and a solution of 4-methoxybenzoyl chloride (1.58 L) in heptane (1.3 L) was added over 10-20 min. A solution of diethylaluminum chloride (1.8 M, 10.8 L) was added over 30 min at 0-5° C. Upon complete addition the reaction was warmed to rt. 6M HCl in water (2.12 L) was slowly added over 30 min to quench the reaction. The resultant slurry was warmed to rt, heptane (49 L) was added, the mixture was aged 1-2 hrs at rt and then filtered. A reverse quench may alternatively be used in which the reaction is added to a mixture of cold water and heptane. After drying the collected solid under a stream of nitrogen overnight, the material was taken up in ethanol (17.3 L), the slurry was heated to reflux and 3M HCl in water (7.4 L) added. The solution was cooled to rt and the resultant slurry filtered, washed with 30% 3M HCl in ethanol, then dried under a stream of nitrogen to afford the crystalline acylated product 9. The product is further purified by a single recrystallization from toluene.

Step 8A:

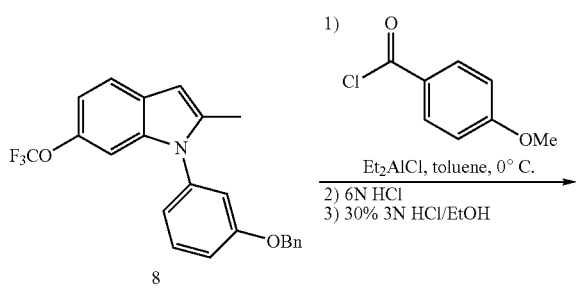

Step 8a: (S) Isobutyl 2-hydroxybutyrate

A vessel was charged with potassium dihydrogen phosphate (1.40 Kg) and water (70.2 L), and the pH was adjusted to 7.5 by addition of concentrated sulfuric acid. Sodium formate (1.54 Kg), and a solution of 2-ketobutyric acid potassium salt (2 Kg) in water (8 L) was added followed by β-nicotinamide adenine dinucleotide (96.3 g) and formate dehydrogenase (35.5 g). The mixture was stirred at 31-37° C. and the pH of the solution adjusted to 7.4 by addition of sodium hydroxide. L-lactic dehydrogenase type VIII from chicken heart enzyme solution (150 mg) was added, and the reaction was aged for 18 h with stirring at 33-38° C. and pH control (7.4-7.6) using sulfuric acid solution. Alternatively, this reaction can be carried out using glucose dehydrogenase rather than formate dehydrogenase to carry out the reduction of the stoichiometric reducing agent so that it is recycled.

After complete conversion, isobutyl alcohol (40 L) and potassium chloride (5 Kg) were added followed by sulfuric acid to adjust the pH to 2. The aqueous layer was extracted with isobutyl alcohol (3×40 L). The combined extracts were concentrated to approx 20% volume, concentrated sulfuric acid (5 mol %) was added, and the solution was aged for 12 h to complete the esterification. The solution was washed with aqueous 10% potassium bicarbonate (10 L). N-methylmorpholine can be used in place of the 10% potassium bicarbonate in this workup. The phases were separated and the organic layer was washed with water (10 L). Concentration using a fractional distillation column and a solvent switch to toluene at reduced pressure afforded crude (S) isobutyl 2-hydroxybutyrate as a 25% solution in toluene, which was used without further purification.

Step 8B: (S) Isobutyl 2-tosyloxybutyrate

To a solution of (S) isobutyl 2-hydroxybutyrate (2.72 Kg) and p-toluenesulfonylchloride (3.6 Kg) in ethyl acetate (14 L) at 20° C. was added a solution of DABCO (286 g) and triethylamine (4.7 L) in ethyl acetate (10 L) over 2 h. The reaction was aged at 20-25° C. for 4 h. The mixture was washed with three times with water (10 L, 2 L and 2 L) and the organics concentrated and solvent switched into toluene. The concentrated toluene solution of (S) 2-isobutyl tosylbutyrate was used as is in coupling reaction. Alternatively, acetonitrile can be used in place of ethyl acetate, in which case the reaction proceeds faster.

Step 9: Acylation

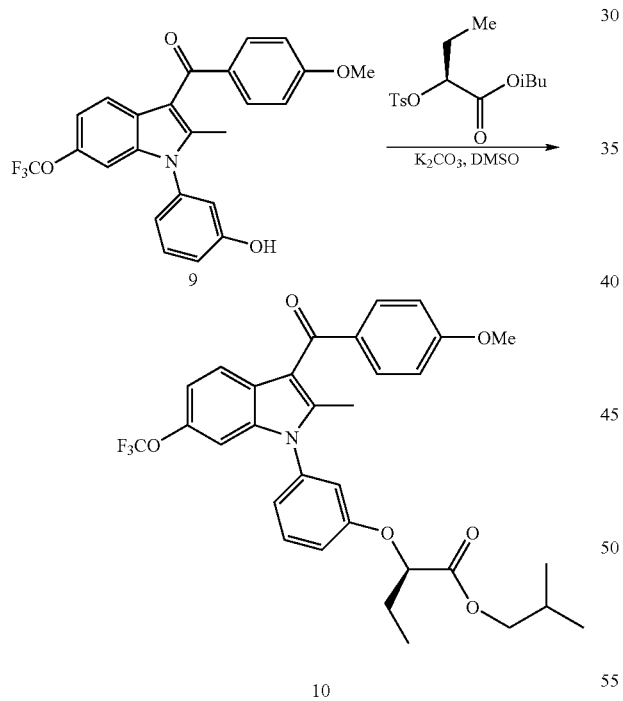

A 50 L vessel fitted with a mechanical stirrer, a thermometer probe, nitrogen inlet and an addition funnel was charged with DMSO (6 L), (S) 2-isobutyl tosyloxybutyrate (1.70 Kg) and indole-phenol 9 (2.04 Kg) at 20° C. under nitrogen. Powdered potassium carbonate (1.88 Kg) was added. DMSO (2 L) was used to rinse the materials into the vessel. The resultant slurry was stirred at 28-30° C. for 24 h. On complete reaction MTBE (10 L) was added and the slurry cooled to 10° C. Water (15 L) was added and the phases well mixed at rt (20-25° C.). The lower aqueous layer was removed. The organics were washed with 0.2M KHCO₃ (2×5 L). The crude product 10 was used without purification in the hydrolysis step.

Step 10: Hydrolysis

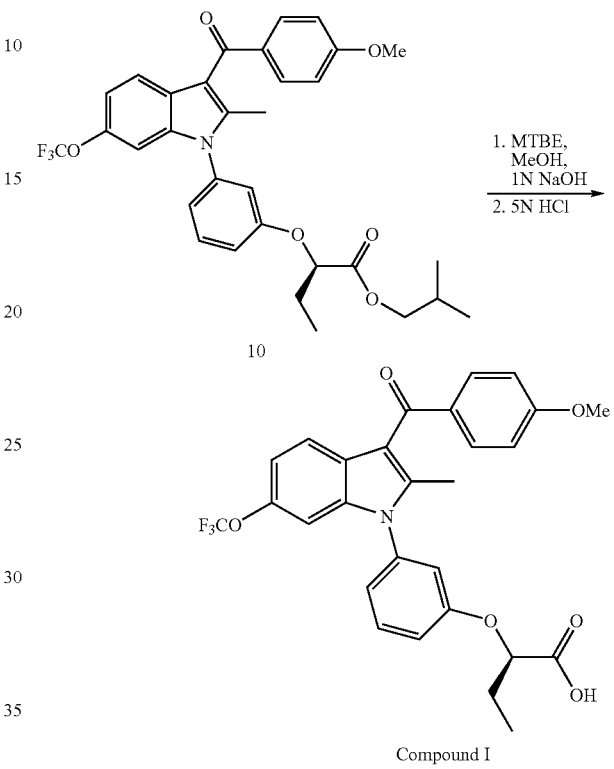

Compound I

A solution of ester 10 (8.98 kg) in MTBE was diluted with methanol (27 L). 1M Sodium Hydroxide (30.8 L) was added at ambient temperature. The biphasic reaction mixture was vigorously agitated at 40 ° C. for 2 h. Longer reaction times (~16 hr at 40° C.) are required depending on the amount of residual toluene from the coupling reaction with (S) 2-isobutyl tosyloxybutyrate (step 9). The reaction mixture was cooled to ambient temperature and diluted with MTBE (22 L). 5M Hydrochloric acid (26.8 L) was added with vigorous stirring. The organic layer was washed with water (3×20 L). The organic layer was concentrated to about ⅓ of its original volume, flushed with toluene to remove residual MTBE, and diluted with toluene to a total batch volume of about 40 L. Water (1 L) was added to the solution with vigorous stirring. The biphasic mixture was aged at ambient temperature (18-23° C.) for a few minutes and seeded with Compound I dihydrate seed (Example 4). The slurry was stirred vigorously at room temperature (18-23° C.) for 5 h. Heptane (51.5 L) was added over 2-4 h at ambient temperature with stirring. The batch was filtered and the wet cake washed with 1:1 toluene/heptane (15 L) followed by heptane (15 L) and dried under dry nitrogen at 40-50° C. to give Compound I free acid anhydrate as a white crystalline solid. The solid anhydrate obtained above is hydrated to the crystalline dihydrate by placing it under a flow of wet nitrogen (RH>70%, non-condensing).

EXAMPLE 2

Preparation of the Crystalline Anhydrate and Dihydrate of Compound I

Compound I hydrate and anhydrate are readily interconverted. Compound I dihydrate from Example 1 or crude or pure Compound I dihydrate from other sources as a free acid can be made into the crystalline anhydrate and converted back to the crystalline dihydrate as follows. Compound I (7.57 kg assay, 14.4 moles) is dissolved in enough dry toluene to make a solution having a total volume of 30.3 L (4.0 L toluene solution/Kg of Compound I).

Water (1.03 L; 1.03 kg; 57.4 moles; 4.00 equiv) is added to the solution with vigorous stirring. The biphasic mixture is aged at ambient temperature (18-23° C.) for a few minutes and is then seeded with Compound I dihydrate seed (67 g, 0.12 moles, 0.0083 equiv). The batch turns hazy after the seeding. Solid gradually precipitates out to give a thick slurry.

The slurry is stirred vigorously at room temperature (18-23° C.) until supernatant equilibrium is reached (60-80 mg/ml of Compound I in toluene).

Heptane (51.5 L; 35.2 kg) is then added over 2-4 h at ambient temperature with stirring. The resulting mixture is stirred at ambient temperature until supernatant equilibrium is reached (typically <7 mg/ml of Compound I).

The batch is filtered at ambient temperature. The wet cake is washed with 1:1 toluene/heptane wash (15.1 L) followed by a heptane wash (15.1 L), and is then dried under dry nitrogen at about 40-50° C. to give Compound I free acid anhydrate as a white crystalline solid.

The solid is rehydrated to the crystalline dihydrate form under a flow of wet nitrogen (RH>70%, non-condensing). A typical yield of solid Compound I dihydrate by this procedure is 7.9 Kg (14.0 mol, 97% yield) with >99 Assay % chemical purity and >99.8% ee.

EXAMPLE 2A

An alternate procedure for purifying Compound II dihydrate is presented below. The scale is 120 gm of dihydrate.

Dihydrate (120 g) and isopropyl alcohol (IPA; 540 mL) are charged into a crystallizer. The mixture is heated to 38-40° C. to dissolve the dihydrate. Deionized water (273 mL) is added over ~10 minutes to bring the batch to 33.6 v % water. The batch temperature is adjusted to 38-40° C. Then 120 g of 60/40 v/v deionized water/IPA media milled seed slurry (50 mg dihydrate/g slurry) is added. This provides 6 g dihydrate (5%), 74.8 mL deionized water, and 49.9 mL IPA, so that the batch contains 37.1 v % water.

Then 30 g of 60/40 v/v deionized water/IPA is added as a follow flush. The batch now contains 37.9 v % water. The seed bed is aged for 1 hr at 38-40° C. Deionized water (537 mL) is then added in two equal portions, the first portion over 6 hrs and the second portion over 9 hrs, while maintaining the temperature of the batch at 38-40° C. This brings the batch to 60/40 v/v deionized water/IPA.

The batch is cooled gradually to 15-20° C. over 1.5 hrs. It is then aged for 1 hr and filtered. The cake is washed with two 480 mL portions of deionized water. The wet filter cake is then dried in a humid atmosphere with a 40° C. jacket temperature.

EXAMPLE 3

Preparation of the Crystalline Anhydrate of Compound I

Crystalline anhydrate is made by warming the crystalline dihydrate to 40-50° C. under dry nitrogen as described in Examples 1 and 2.

EXAMPLE 4

Preparation of Seed Crystals of Compound I Dihydrate

The crude acid form of Compound I (7.6 g) is dissolved in toluene (30 mL) and treated with water (1.0 mL). The resulting two-phase mixture is stirred vigorously at ambient temperature for 2 h. The mixture is allowed to stand at 5° C. for 2 days. The small amount of crystals at the interface are filtered and used as seed crystals for larger batches of Compound I dihydrate.

Characterization of the Anhydrate and Dihydrate

X-ray powder diffraction studies are widely used to characterize molecular structures, crystallinity, and polymorphism. The X-ray powder diffraction patterns of the dihydrate and anhydrate were generated on a Philips Analytical X'Pert PRO X-ray Diffraction System with PW3040/60 console. A PW3373/00 ceramic Cu LFF X-ray tube K-Alpha radiation was used as the source. The X-ray powder diffraction spectrum was recorded at ambient temperature (CuKα radiation, 2° to 40° (2θ), steps of 0.0167°, 5.08 sec per step).

FIG. 1 shows a characteristic X-ray powder diffraction pattern of Compound I dihydrate. The dihydrate is characterized by peaks at 16.8°, 19.6° and 5.7° 2θ. The dihydrate can be further characterized by peaks at 22.4°, 7.7° and 15.2° 2θ. It can be further characterized by peaks at 24.6°, 11.2° and 22.8° 2θ.

Figure 6:
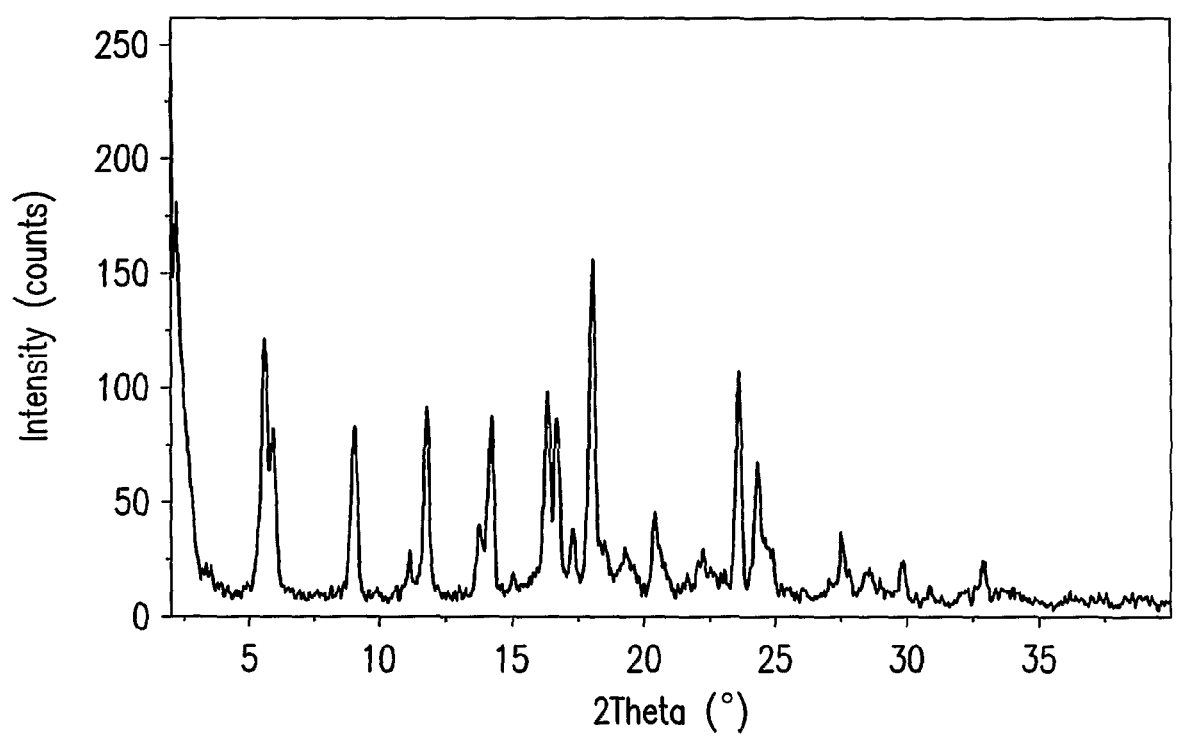
FIG. 6 provides a characteristic X-ray powder diffraction pattern of Compound I crystalline anhydrate.

FIG. 6 shows a characteristic X-ray powder diffraction pattern of Compound I anhydrate. The anhydrate is characterized by peaks at 18.1°, 11.9° and 9.1° 2θ. The anhydrate can be further characterized by peaks at 14.3°, 16.4° and 23.7° 2θ. It can be further characterized by peaks at 5.9°, 13.8° and 20.5° 2θ.

The crystal forms were also characterized by thermogravimetric analysis using a Perkin Elmer model TGA 7 instrument to generate the TGA curves. Experiments were performed under a flow of nitrogen and using a heating rate of 10° C./min. Weight/temperature data were collected automatically by the instrument. Analysis of the results was carried out by selecting the Delta Y function within the instrument software and choosing the temperatures between which the weight loss was to be calculated. Weight losses are reported up to the onset of decomposition/evaporation.

Figure 2:
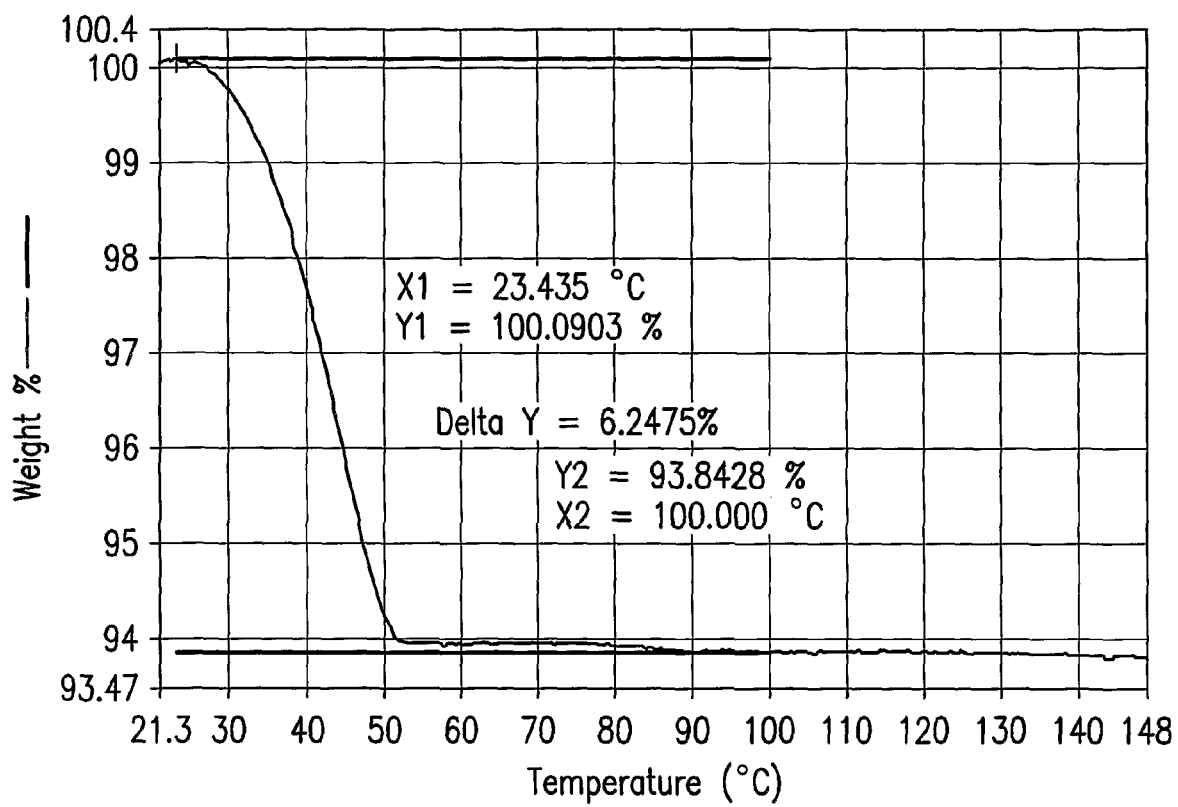
FIG. 2 provides a characteristic thermogravimetric analysis (TGA) curve of Compound I crystalline dihydrate.

FIG. 2 shows a characteristic thermogravimetric analysis (TGA) curve of Compound I dihydrate under a nitrogen flow at a heating rate of 10° C./min. Weight loss of 6.25% occurs between 21° C. and 55° C. This weight loss is in agreement with the predicted weight change for the loss of 2 moles of water from the dihydrate of Compound I (theoretical weight loss is 6.4%).

The water content of the dihydrate was also measured by Karl Fischer titration The water content of the dihydrate was measured as 6.6%, compared with a theoretical water content of 6.4%.

Figure 7:
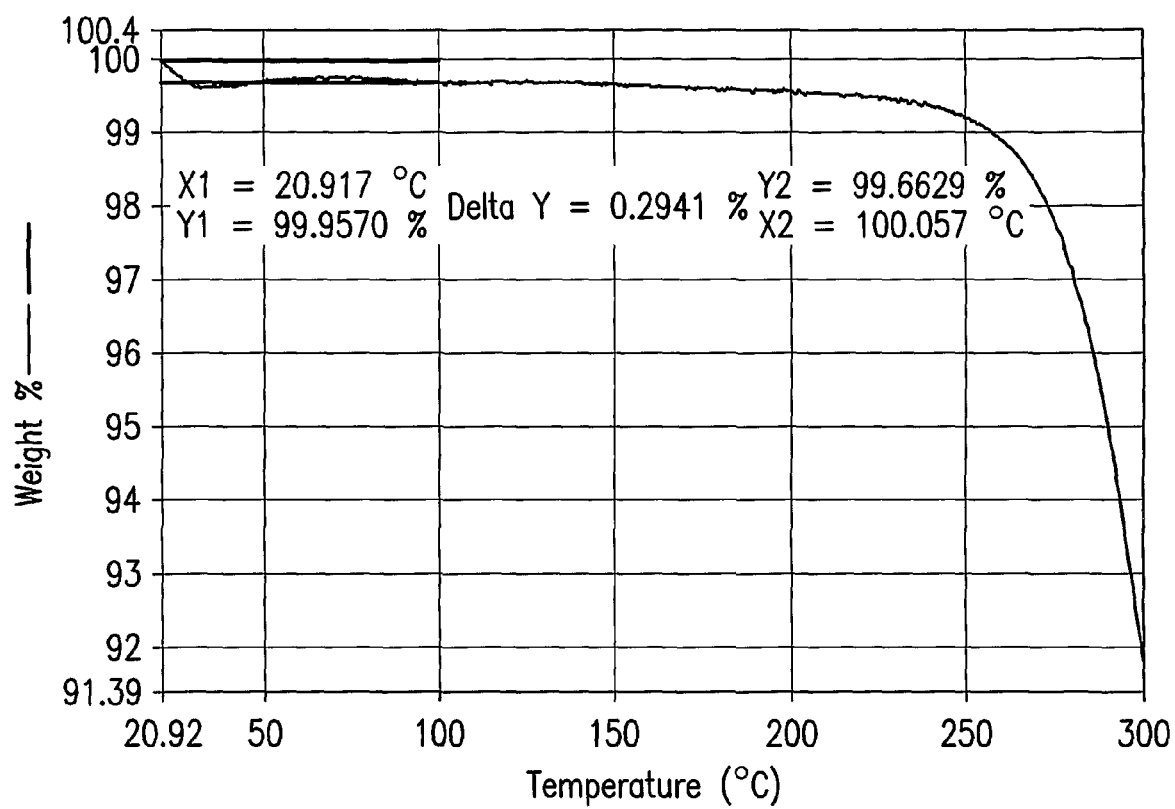
FIG. 7 provides a characteristic thermogravimetric analysis (TGA) curve of Compound I crystalline anhydrate.

FIG. 7 shows a characteristic thermogravimetric analysis (TGA) curve of Compound I anhydrate under a nitrogen flow at a heating rate of 10° C./min. A weight loss of 0.3% in the range of 20.9-100.1° C. indicates that the compound is anhydrous.

Figure 3:
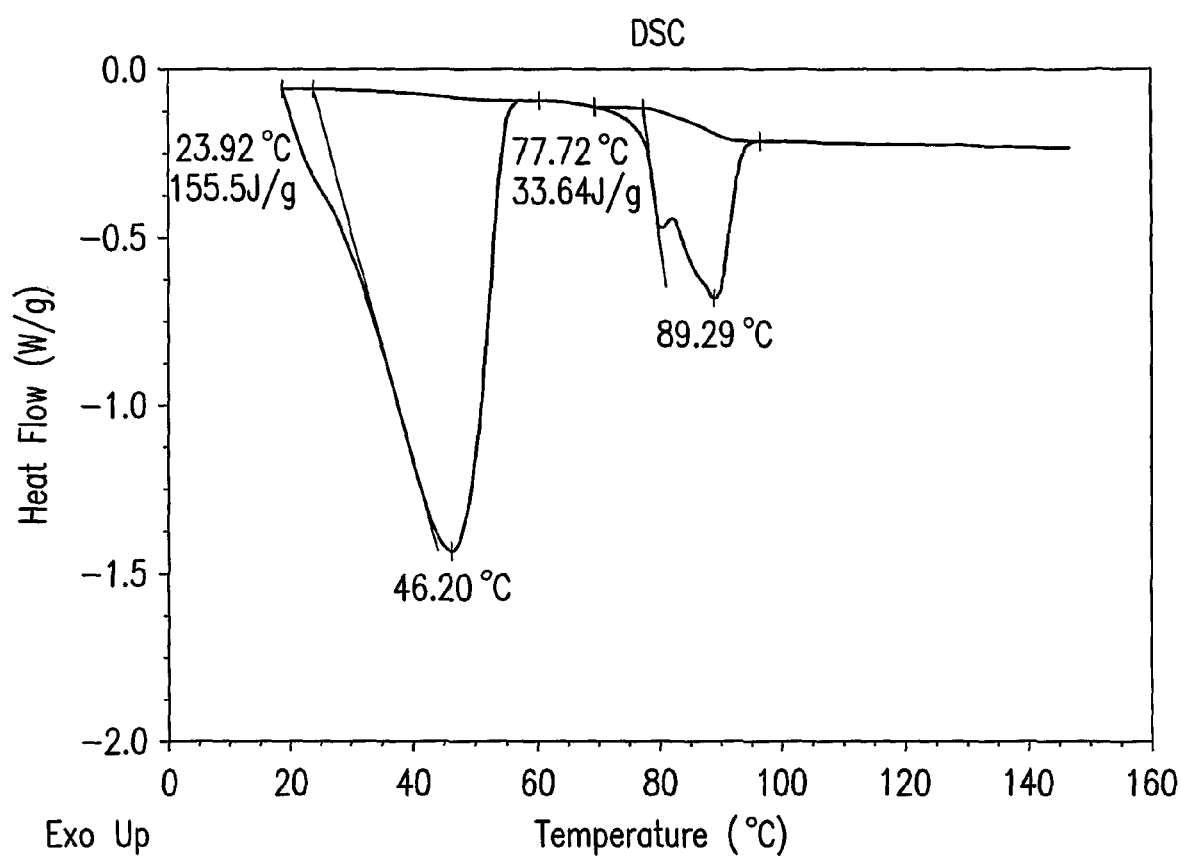
FIG. 3 provides a characteristic differential scanning calorimetry (DSC) curve of Compound I crystalline dihydrate.

FIG. 3 shows a characteristic differential scanning calorimetry (DSC) curve for Compound I dihydrate. This was obtained using a TA Instruments DSC 2910 differential scanning calorimeter. The sample was heated in a closed pan under nitrogen flow at a heating rate of 10° C./min. The data were analyzed using the DSC analysis program contained in the system software. The melting endotherm was integrated between baseline temperature points that are above and below the temperature range over which the endotherm was observed. The data reported are the onset temperature, peak temperature and enthalpy.

Figure 8:
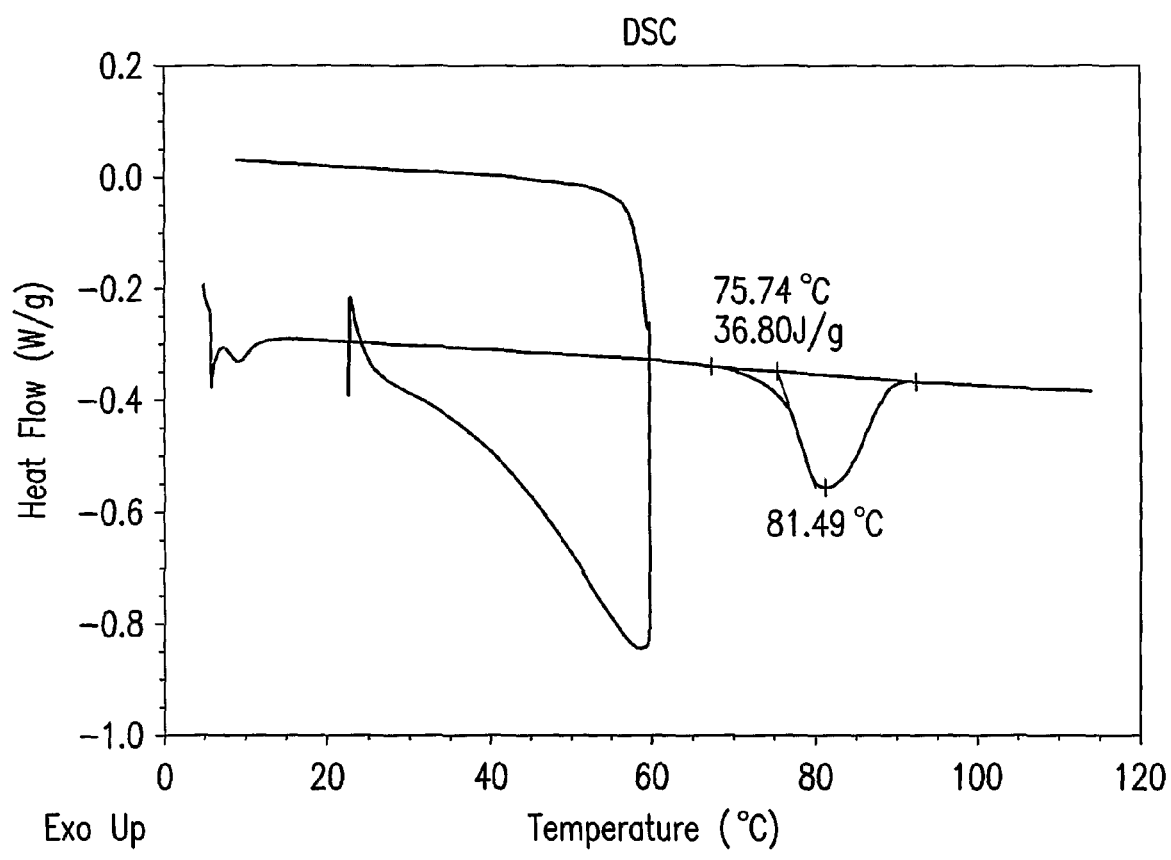
FIG. 8 provides a characteristic differential scanning calorimetry (DSC) curve of Compound I crystalline anhydrate.

FIG. 8 shows a characteristic differential scanning calorimetry curve for Compound I anhydrate. The DSC curve was obtained using a TA Instruments Q1000 differential scanning calorimeter under the following conditions: (1) The sample was first heated to 60° C. at 3° C./min. (2) The sample was held isothermally at 60° C. for 30 min after which it was cooled to 5° C. at 10° C./min. (3) Then a modulated run was performed with a modulation of 1° C. every 60 sec and a linear heating rate of 3° C./min up to 120° C. under $N_2$ flow. The sample was heated in a closed pan.

In addition to the X-ray powder diffraction patterns described above, the crystalline dihydrate form of compound I was further characterized by solid-state carbon-13 and fluorine-19 nuclear magnetic resonance (NMR) spectra. The solid-state carbon-13 NM spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 1777 scans were collected with a recycle delay of 7 seconds. A line broadening of 20 Hz was applied to the spectrum before FT was performed. Chemical shifts are reported on the TMS scale using the carbonyl carbon of glycine (176.03 p.p.m.) as a secondary reference.

The solid-state fluorine-19 NMR spectrum was obtained on a Bruker DSX 400WB NMR system using a Bruker 4 mm CRAMPS probe. The NMR spectrum utilized a simple pulse-acquire pulse program. The samples were spun at 15.0 kHz, and a total of 128 scans were collected with a recycle delay of 2 seconds. A vespel endcap was utilized to minimize fluorine background. A line broadening of 50 Hz was applied to the spectrum before FT was performed. Chemical shifts are reported using poly(tetrafluoroethylene) (teflon) as an external secondary reference which was assigned a chemical shift of −122 ppm.

Figure 4:
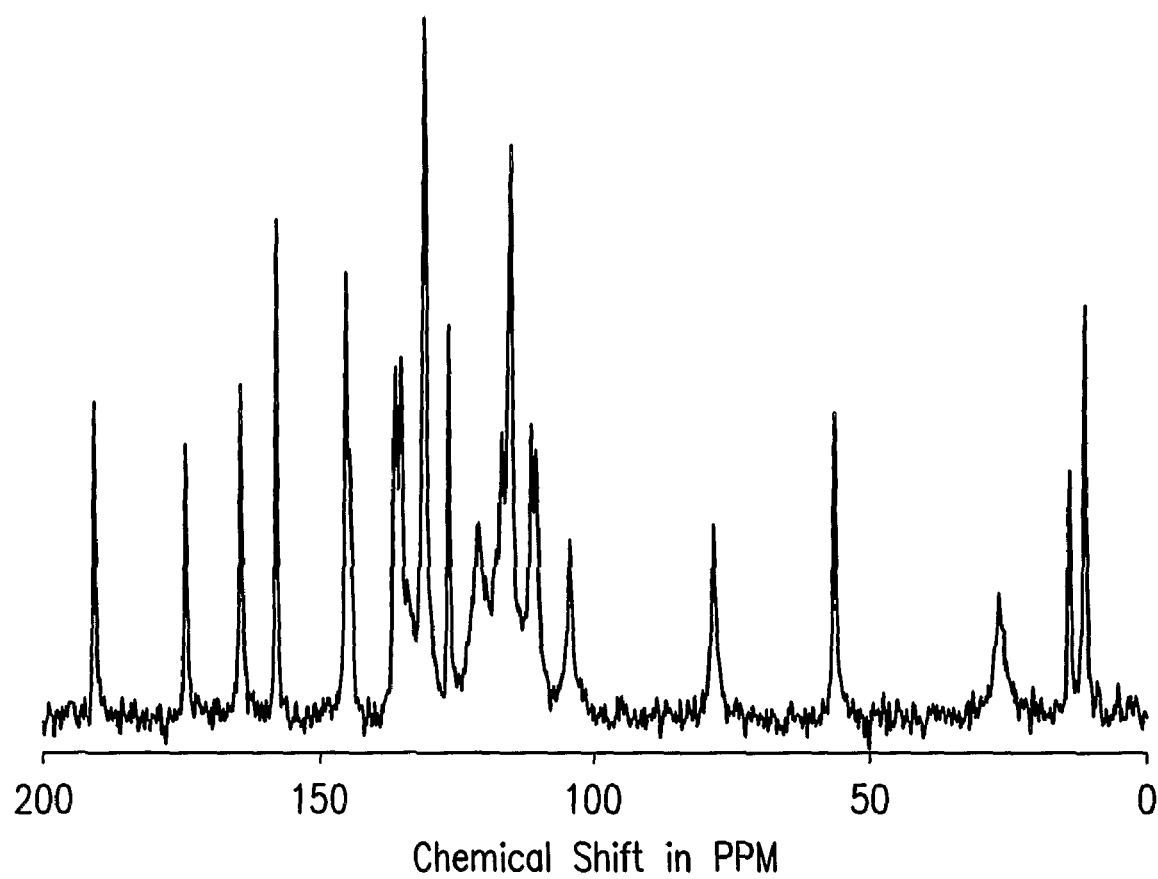
FIG. 4 provides a characteristic solid state carbon-13 CPMAS NMR spectrum for the crystalline dihydrate form of Compound I.

FIG. 4 shows the solid-state carbon-13 CPMAS NMR spectrum for the dihydrate form of compound I. The dihydrate form exhibited characteristic signals with chemical shift values of 11.1, 56.2, 190.7 p.p.m. Further characteristic of the dihydrate form are the signals with chemical shift values of 13.9, 78.3, and 174.2 p.p.m. The dihydrate form is even further characterized by signals with chemical shift values of 164.1, and 157.6 ppm.

Figure 5:
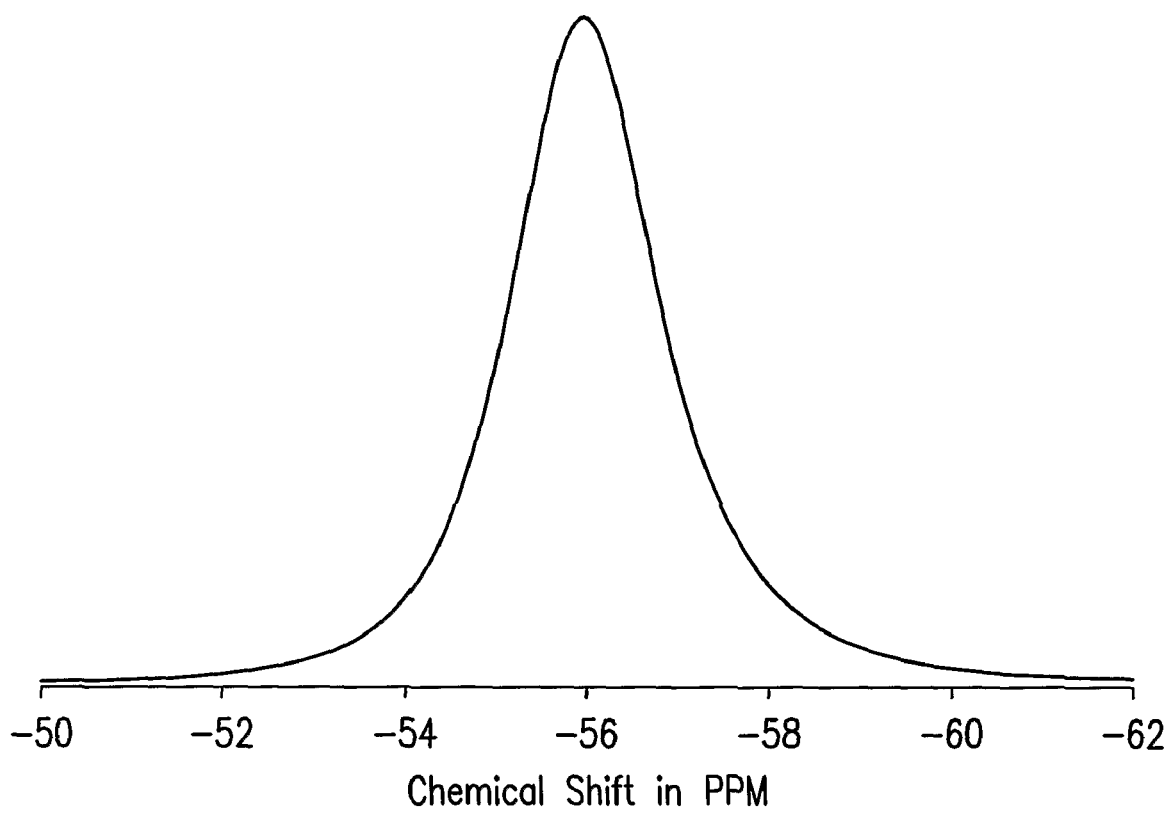
FIG. 5 provides a characteristic solid-state fluorine-19 MAS NMR spectrum for the crystalline dihydrate form of Compound I.

FIG. 5 shows the solid-state fluorine-19 MAS NMR spectrum for the dihydrate form of compound I. The dihydrate form exhibited a characteristic signal with chemical shift value of −56.0 ppm.

Figure 9:
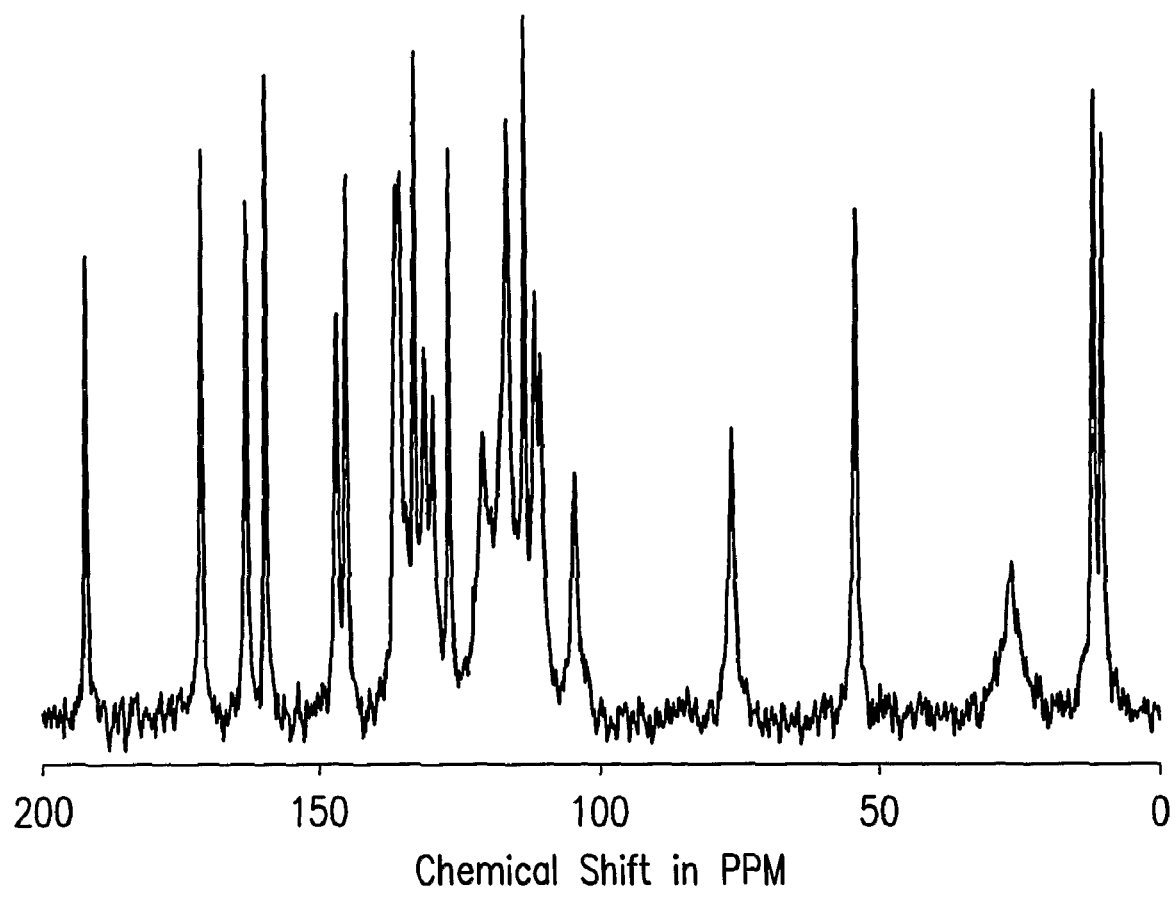
FIG. 9 provides a characteristic solid state carbon-13 CPMAS NMR spectrum for the crystalline anhydrate form of Compound I.

FIG. 9 shows the solid-state carbon-13 CPMAS NMR spectrum for the anhydrate form of compound I. The anhydrate form exhibited characteristic signals with chemical shift values of 10.3, 54.1, and 192.2 p.p.m. Further characteristic of the anhydrate form are the signals with chemical shift values of 11.9, 76.3, and 171.2 p.p.m. The anhydrate form is even further characterized by signals with chemical shift values of 163.0 and 159.3 ppm.

Figure 10:
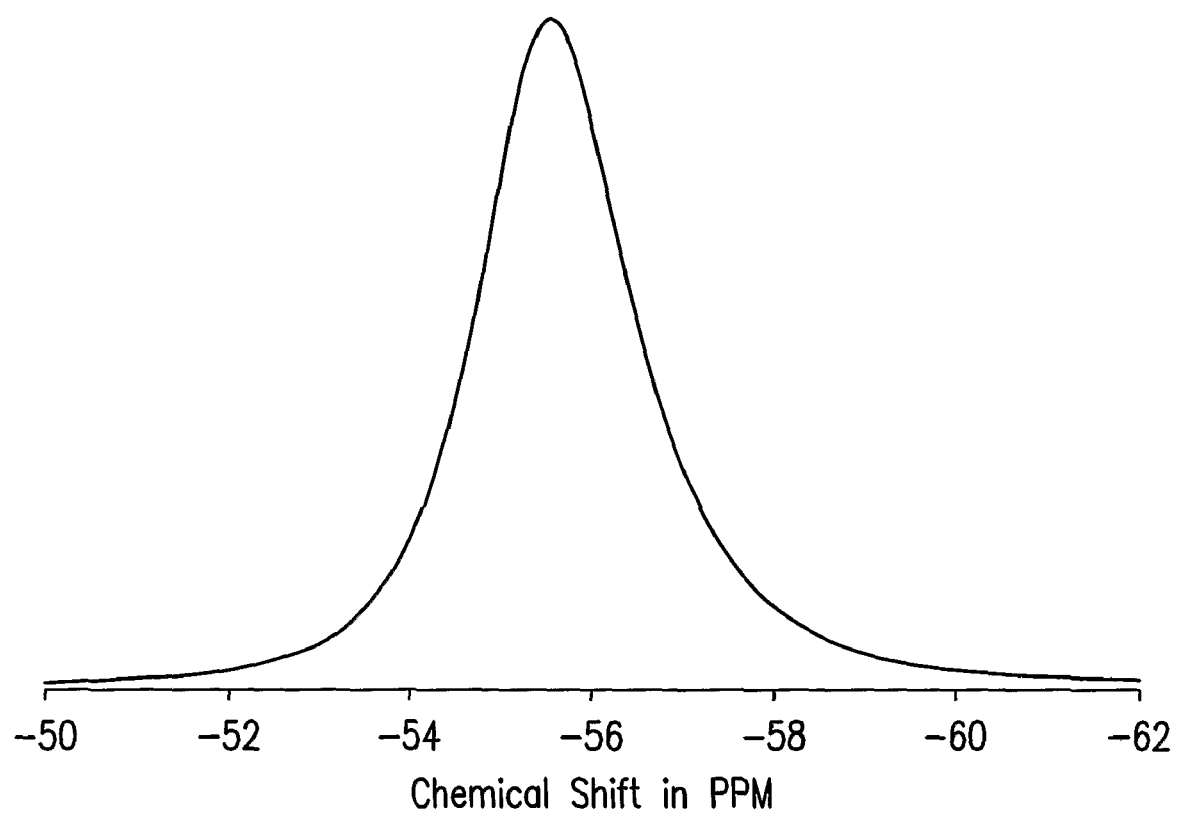
FIG. 10 provides a characteristic solid-state fluorine-19 MAS NMR spectrum for the crystalline anhydrate form of Compound I.

FIG. 10 shows the solid-state fluorine-19 MAS N spectrum for the anhydrate form of compound I. The anhydrate form exhibited a characteristic signal with chemical shift value of −55.6 ppm.

The crystalline Compound I dihydrate and the crystalline Compound I anhydrate form of the present invention each has a phase purity of at least about 5% of dihydrate or anhydrate with the above X-ray powder diffraction, fluorine-19 MAS NMR, carbon-13 CPMAS NMR, and DSC physical characteristics. In one embodiment the phase purity is at least about 10% of dihydrate or anhydrate with the above solid-state physical characteristics. In a second embodiment the phase purity is at least about 25% of dihydrate or anhydrate with the above solid-state physical characteristics. In a third embodiment the phase purity is at least about 50% of dihydrate or anhydrate with the above solid-state physical characteristics. In a fourth embodiment the phase purity is at least about 75% of dihydrate or anhydrate with the above solid-state physical characteristics. In a fifth embodiment the phase purity is at least about 90% of dihydrate or anhydrate with the above solid-state physical characteristics. In a sixth embodiment the crystalline Compound I is the substantially phasepure dihydrate or anhydrate with the above solid-state physical characteristics. By the term "phase purity" is meant the solid state purity of the Compound I anhydrate or dihydrate form with regard to another particular crystalline polymorph or amorphous form of Compound I as determined by the solid-state physical methods described in the present application.

EXAMPLE 5

Synthesis of (2R)-2-{3-[[3-(4-chlorobenzoyl)-2-methyl-6-(trifluoromethoxy)-1H-indol-1-yl]methyl]phenoxy}butyric acid (Compound II)

Steps 1-4 are the same as Steps 1-4 of Example 1.

Step 5

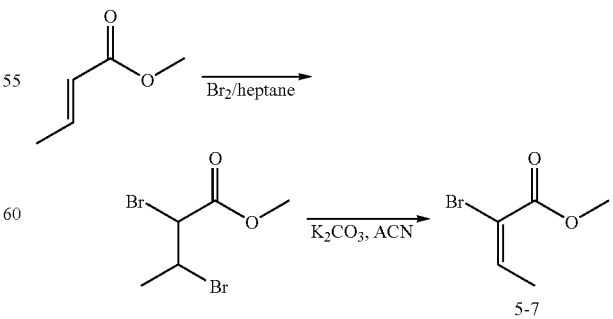

A solution of methyl crotonate (3.00 Kg) in heptane (9.0 L), under nitrogen, was treated with bromine (1.55 L) at 25 to 35° C. over 20-30 min. The reaction mixture was stirred at 30° C. for 1 h. Acetonitrile (18 L) was added followed by powdered potassium carbonate (6.08 Kg) in one portion. The reaction slurry was warmed and stirred at 60° C. for 1 h and then was heated to reflux (74° C. batch temp). The heptane/acetonitrile azeotrope (b.p. 69° C.) was distilled off, with removal of 15 L of solvent. Acetonitrile (ACN, 6 L) was added during the atmospheric distillation. On complete distillation the slurry was aged at 80° C. for 3-4 h to complete the dehydrobromination. On complete reaction, the slurry was cooled to 20° C. and filtered. The cake was washed with acetonitrile (2×6 L). The solution of product 5-7 was used without further purification in the alkylation reaction.

Step 6

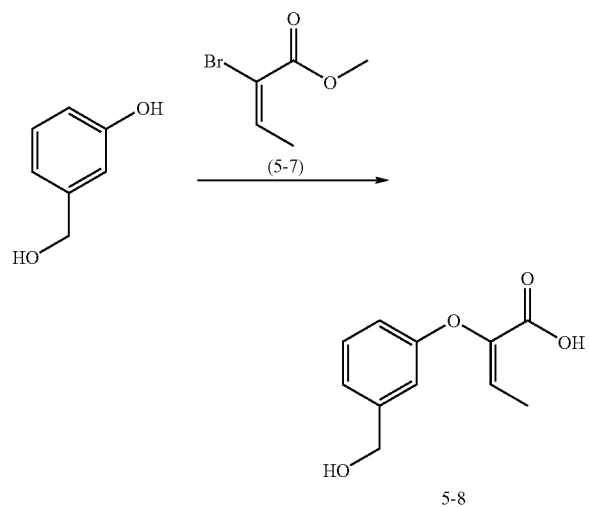

A solution of methyl 2-bromobut-2-enoate 5-7 (20.9 Kg) and 3-hydroxybenzyl alcohol (3.00 Kg) in acetonitrile was treated with powdered potassium carbonate (6.54 Kg), and the slurry was warmed to 80-82° C., over 1 h. The slurry was aged at 80-82° C. for 2 h. Acetonitrile (10 L) was distilled off over 2 h at atmospheric pressure. The reaction mixture was cooled to 50° C., and toluene (20 L) was added. The slurry was concentrated at 30-40° C. under reduced pressure to remove a total of 25 L distillate. Toluene (10 L) was added, and the slurry was cooled to 15° C. Water (20 L) was added, and the phases were well mixed. Water (7.5 L) and 50% w/v aq KOH (5.31 L) were added. The two-phase mixture was stirred and warmed to 35° C. for 5-10 h. The mixture was cooled to 20° C., and the layers were separated. The lower layer (aqueous layer) was charged to a 50 L reaction vessel and was cooled to 15° C. Concentrated hydrochloric acid (2.25 L) was added to adjust pH to 8-9. IPAC (25 L) was added and the pH was adjusted to 1.5 (+/−0.2) with concentrated hydrochloric acid (2.25 L). The lower aqueous layer was removed. The organics were washed with water (2×3.0 L).

The IPAC solution of unsaturated acid was concentrated at 20-30° C. under reduced pressure, and the solvent was switched to toluene. The volume was adjusted to about 30 L. The slurry was aged at 20° C. for 30 min and filtered. The cake was washed with toluene (20 L) and was dried under $N_2$ flow on the filter funnel overnight to provide the crystalline product 5-8.

Step 7

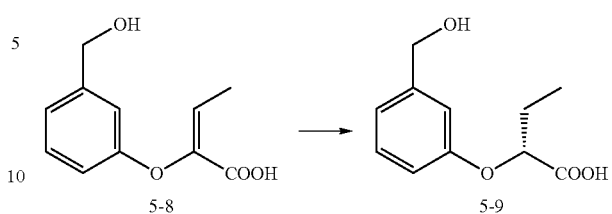

The unsaturated acid 5-8 (3.922 kg), triethylamine (2.63 L), and MeOH (13.4 L) were charged to a 10 gallon autoclave. MeOH (1 L) was used to complete the transfer. A slurry of (R-BINAP)RuCl$_2$ (76.4 g) in methanol (800 mL) was added via a 1 L stainless steel bomb under nitrogen. The batch was hydrogenated at 100 psi hydrogen and 20° C. for 20 h. The batch was filtered through a 5 micron in-line filter, concentrated and solvent switched to toluene. Water (8 L) and 5M aq NaOH (4 L) were added, the phases were separated, and the organic phase was washed with water (4 L). The combined aqueous phases were treated with Darco G-60 carbon (400 g) for 1 h at 60° C. The pH of the mixture was adjusted to pH=7 by addition of conc aq HCl (300 mL) and the mixture was allowed to cool to 22° C. overnight (16 h). Solkafloc (200 g) was added and the mixture was filtered through Solkafloc, washing with water (4 L).

The filtrates were cooled to 10° C. and acidified to pH=1 with conc HCl (3.7 L) maintaining temp at 13-18° C. with cooling. The mixture was extracted with IPAc (20 L). The IPAc extracts were washed with brine (2×4 L) and the product was crystallized from a 3:1 mixture of heptane-IPAc. The crystalline product 5-9 was dried under a stream of nitrogen.

Step 8

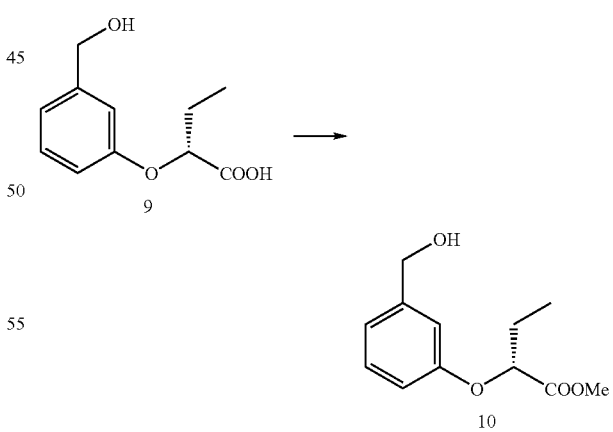

The saturated acid (3.265 kg), TsOH—H$_2$O (58 g) and MeOH (45.7 L) were heated to 60° C. for 14-18 h. Triethylamine (86 mL was added and the mixture concentrated to approximately 10 L. The mixture was solvent switched to isopropyl acetate and the product 5-10 was used without purification in the next step.

Step 9

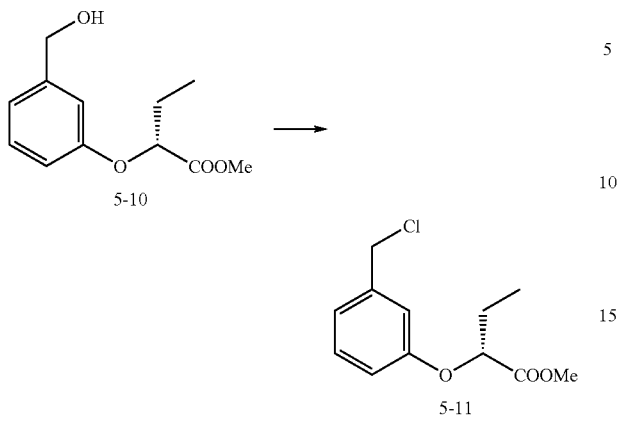

To the crude solution of the methyl ester (3.433 kg) in IPAC (10 L) was added DMF (7.65 L), and the mixture was cooled to −15° C. Thionyl chloride (2.0 Kg) was added to the homogeneous pale amber mixture over 45 min. The mixture was warmed to 20° C. over 30 min and aged for 90 min at 20° C. The mixture was cooled to 0° C. and n-heptane (7.65 L) was added. Water (15.3 L) was added over 5 min with stirring. The aqueous phase was cut and the organics washed with water (2×15 L). The organic phase was concentrated to ca 4 L and the product 5-11 solution used without further purification.

Step 10

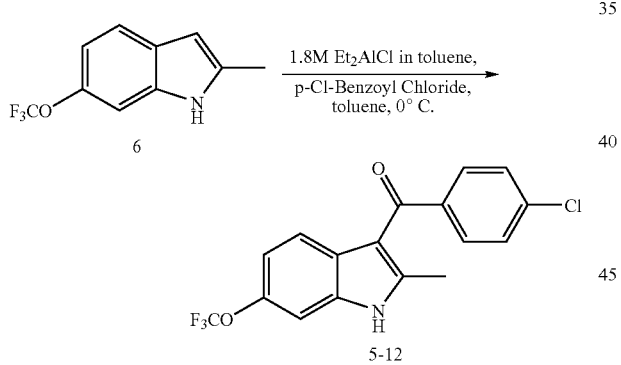

To a solution of the indole product 6 of Step 4, Example 1 (1.98 Kg) in toluene (9 L) at 0° C. was added 1.8 M Et₂AlCl in toluene (6.1 L) over 1-2 h. The resulting solution was stirred for 60 min at 0° C. p-Chlorobenzoylchloride (1.93 Kg) was added as a solution in n-heptane (3 L) over 1-2 hr and the reaction stirred for 12 h. The mixture was cooled to 0° C., and methanol (1.8 L) was added over 1 h. The reaction slurry wa aged for 1 h. n-Heptane (17 L) was added and the resulting slurry aged for 1 h, filtered and the collected precipitate washed with additional n-heptane (22 L).

The red cake was slurried in methanol (61 L) under reflux until all solids dissolve. Water (15 L) was added over 1 h via a dropping funnel to induce crystallization of the product. The resulting slurry was cooled to room temperature, and the product 5-12 was isolated by filtration and dried under a stream of N₂.

Step 11

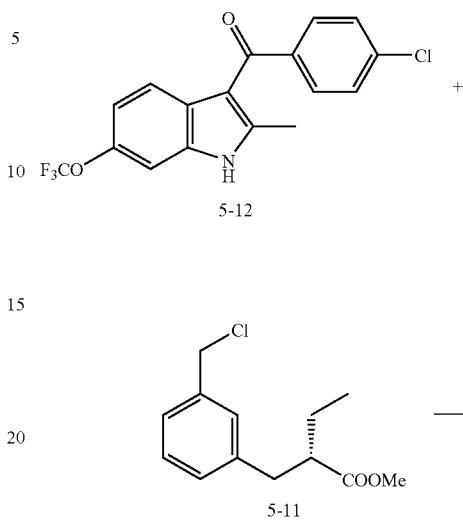

A slurry of acyl indole 5-12 (2.52 Kg), benzyl chloride 5-11 (1.76 Kg), powdered potassium carbonate (1.92 Kg), and nBu₄NI (263 g) in DMF (5.70 L) was stirred at 35° C. for 22 h. The mixture was cooled to 20° C., and then MTBE (4 L) and acetic acid (428 g) were added. MTBE (17.4 L) and water (14 L) were then added and the aqueous phase was cut and discarded. The organic phase was washed with water (21 L). The solution of product 13 in MTBE was used without purification.

Step 12

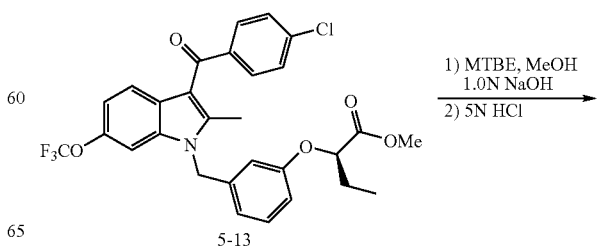

-continued

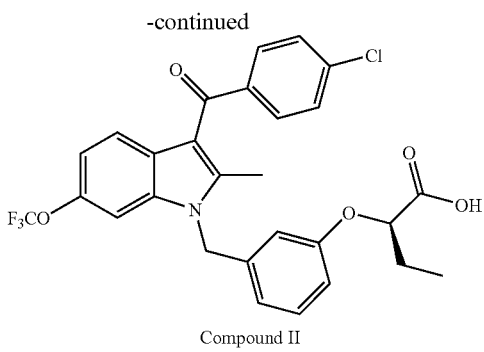

Compound II

Methanol (11.2 L) was added to the crude solution of indole methyl ester 5-13 (3.71 Kg) in MTBE. 1.0 N NaOH (13.25 L) was added at ambient temperature. The resulting reaction mixture was stirred under nitrogen at 40° C. for 4 h. The reaction mixture was cooled to ambient temperature and 5.0 N HCl (2.91 L) was added over 5-10 min with vigorous stirring. The organic layer was washed with water (3×9 L) at 30-35° C. The organic layer was concentrated at reduced pressure and the solvent was switched to toluene (approx 24 L). Heptane (24 L) was added over 30 min, and the resulting slurry was stirred at ambient temperature for 12-14 h. The product was isolated by filtration, and the wet cake was washed with 1:2 toluene/heptane (12 L) followed by heptane (8 L). The crystalline product Compound II was dried under nitrogen at ambient temperature.

EXAMPLE 6

Free acid of Compound II (4 g) is dissolved in IPA (60 mL). 5N Sodium hydroxide (1.46 mL) is added and the slurry is warmed to 55° C. to obtain a homogeneous solution. The solution is cooled to 50° C. and is aged for 1 h to obtain a thin slurry. The slurry is cooled to rt overnight. The slurry is filtered and dried, in vacuo, at 40° C. overnight to provide the sodium salt of Compound II (3.6 g) as fine crystalline needles.

Crystal Forms of Compound II

Compound II as the free acid has at least 3 polymorphic crystal forms, referred to as Forms A, B and C. The sodium salt has at least 5 polymorphic crystal forms, referred to as Forms I, II, III, IV and V. The synthesis described in Example 5 yields Form C free acid, which is a preferred free acid crystalline form. The synthesis described in Example 6 yields Form V sodium salt, which is a preferred sodium salt form.

Form A is prepared by acidification of the sodium salt of Compound II in IPA. The sodium salts of Compound II other than Form V are obtained by suspending sodium salts in various solvents: Forms I and III from suspensions in IPA; Form II from suspensions in α,α,α-trifluorotoluene; and Form IV from THF, AcOEt, and ACN. Form V sodium salt is the most readily obtained. Form C free acid appears to be the most thermodynamically stable acid form.

EXAMPLE 7

Forms B and C Free Acids

Figure 11:
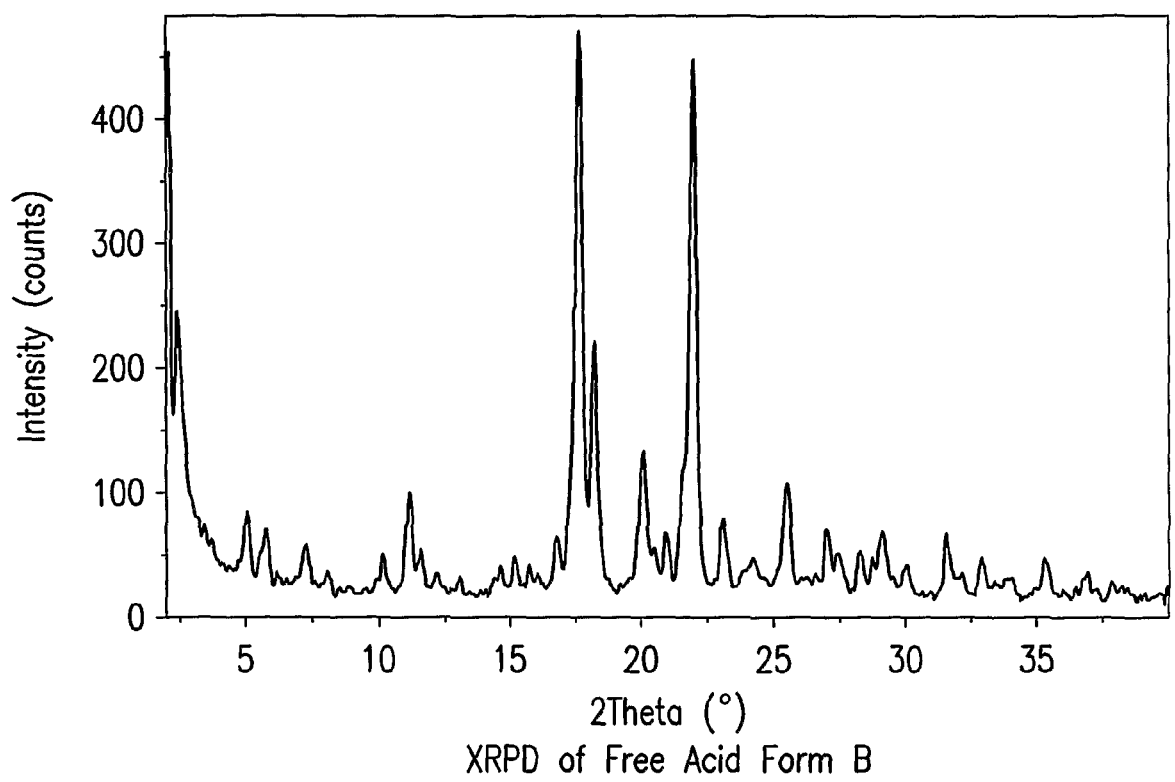
FIG. 11 provides a characteristic X-ray powder diffraction pattern of the Free Acid Form B of Compound II.
Figure 12:
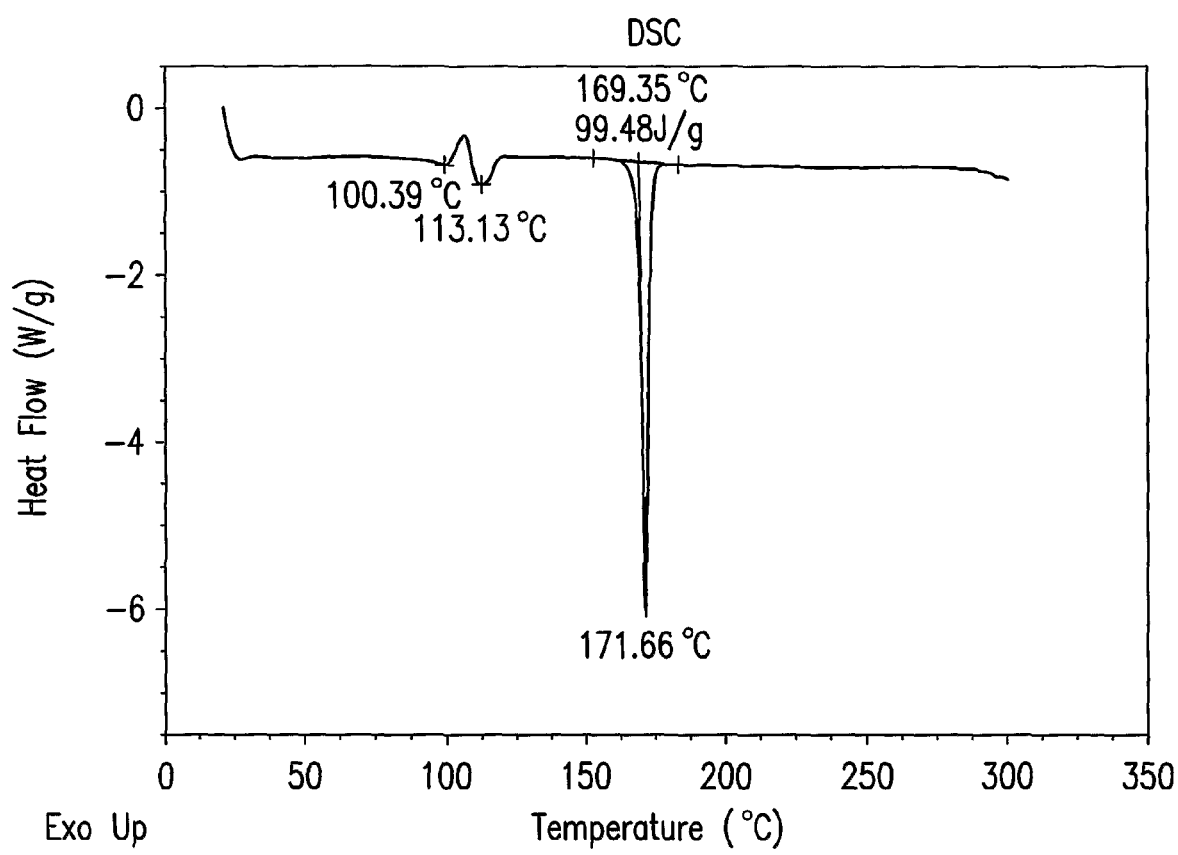
FIG. 12 provides a characteristic differential scanning calorimetry (DSC) curve of the Free Acid Form B of Compound II.
Figure 13:
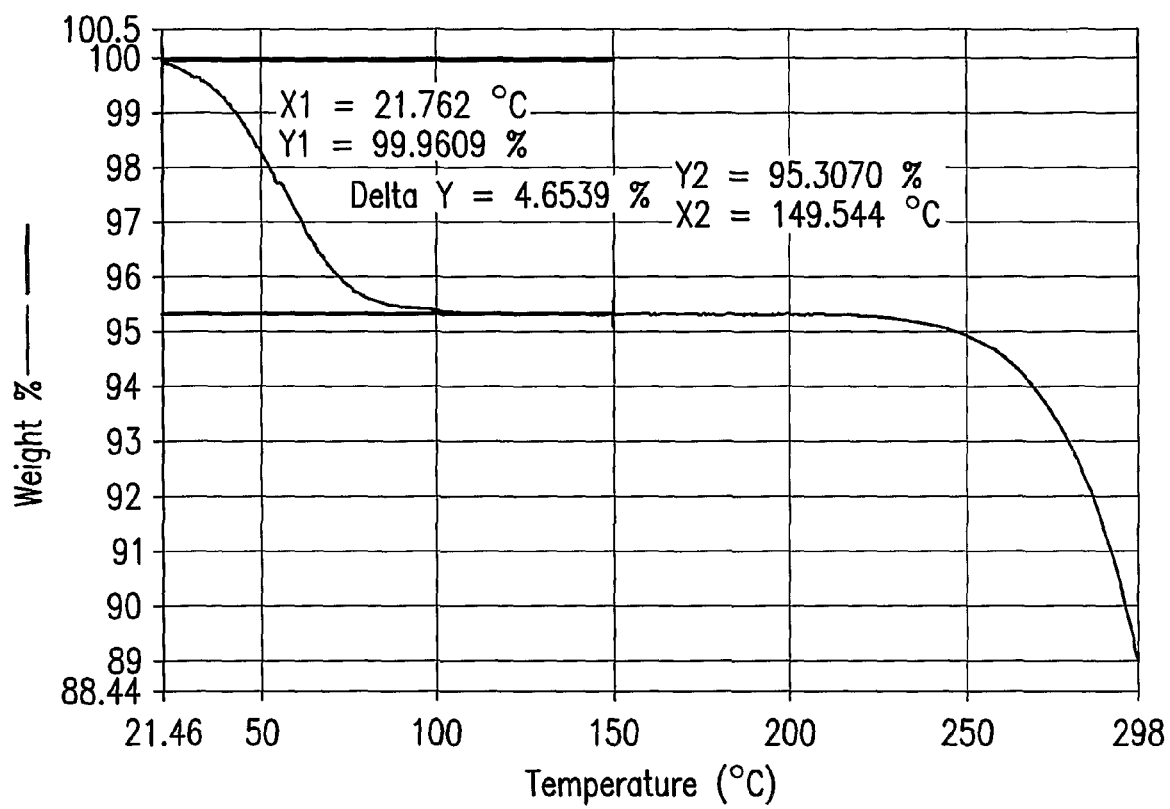
FIG. 13 provides a characteristic thermogravimetric analysis (TGA) curve of the Free Acid Form B of Compound II.
Figure 15:
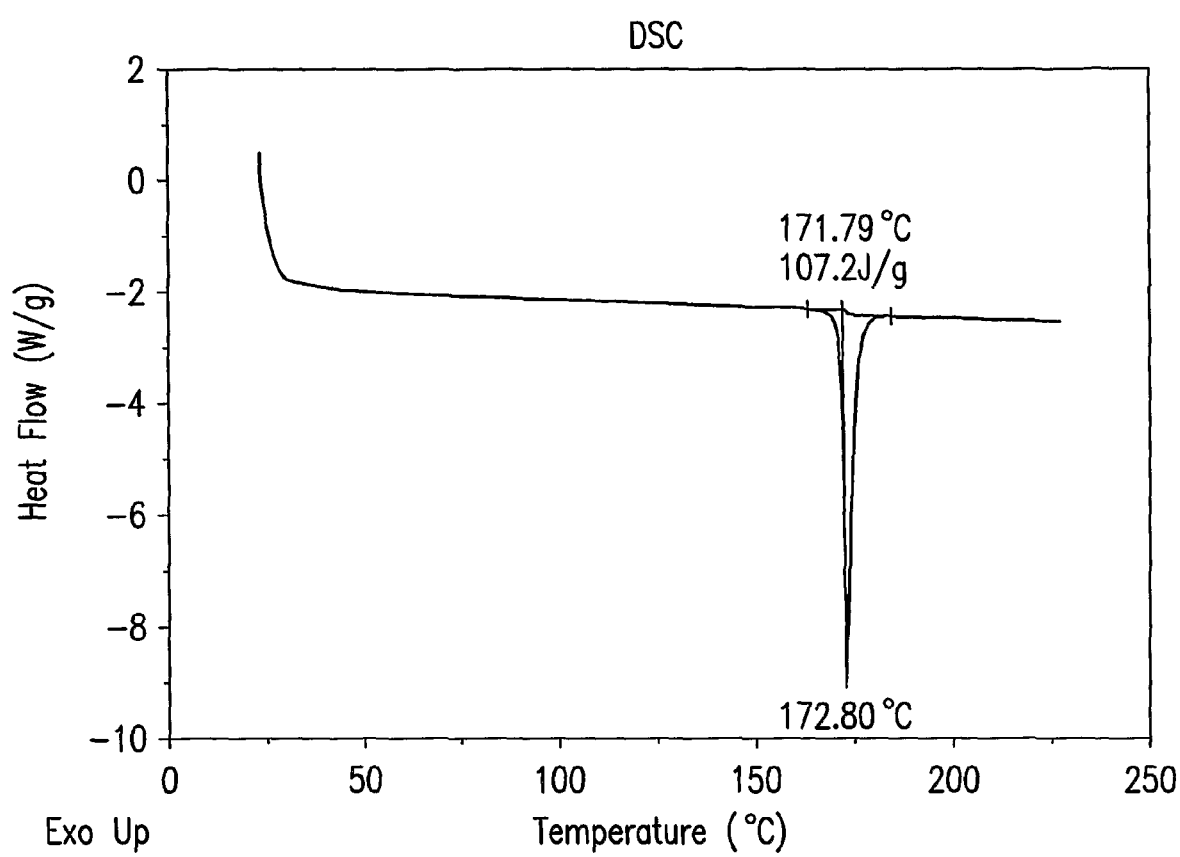
FIG. 15 provides a characteristic differential scanning calorimetry (DSC) curve of the Free Acid Form C of Compound II.

Free Acid Form B is crystalline (FIG. 11) with a DSC curve (FIG. 12) that shows endotherms at 100.4° C. and 113.1° C., which may be due to dehydration and conversion to Form C, followed by melting of Form C (observed in FIG. 15). It has a weight loss (FIG. 13) of 4.7% corresponding to 1.5 moles of water for a mole of free acid (FIG. 3). FIG. 11 shows a characteristic X-ray powder diffraction pattern of crystalline Form B. Crystalline Form B is characterized by peaks at 17.7°, 22.1° and 18.3° 2θ. Crystalline Form B can be further characterized by peaks at 11.2°, 20.1° and 5° 2θ. It can be further characterized by peaks at 5.8°, 10.2° and 25.5° 2θ.

Figure 14:
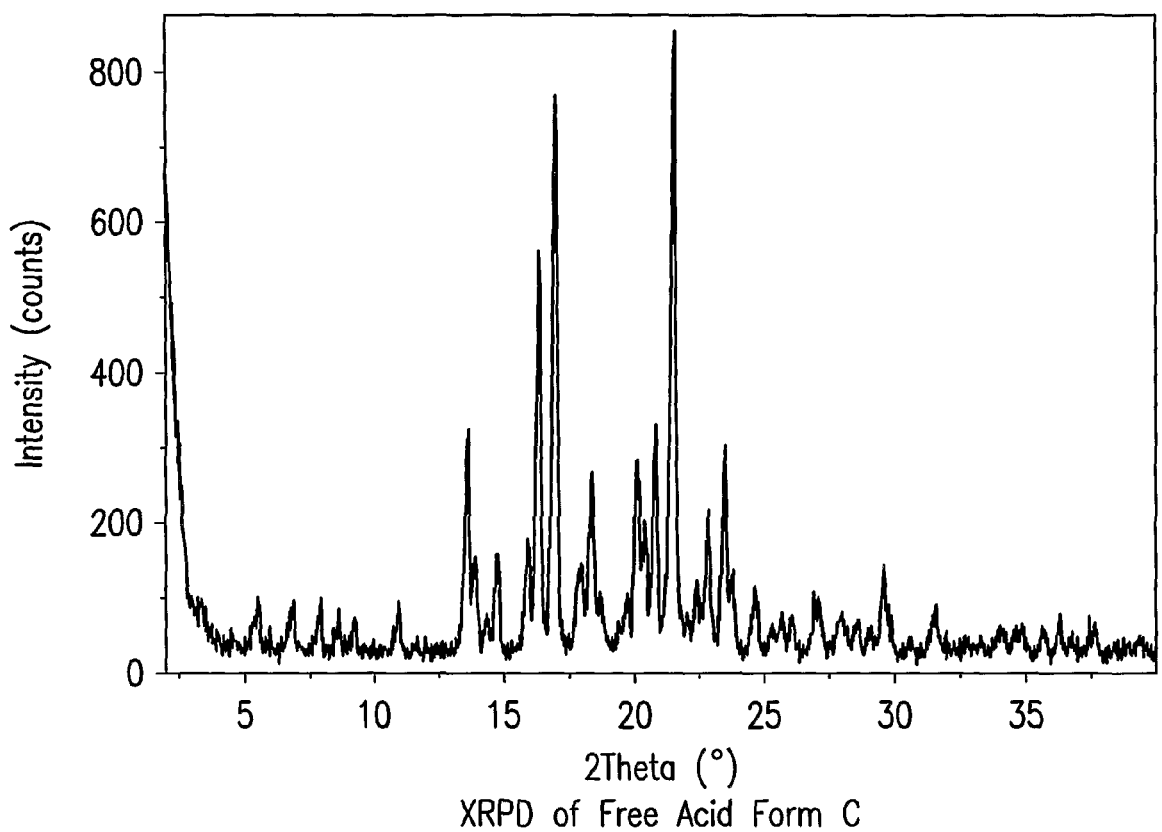
FIG. 14 provides a characteristic X-ray powder diffraction pattern of the Free Acid Form C of Compound II.
Figure 16:
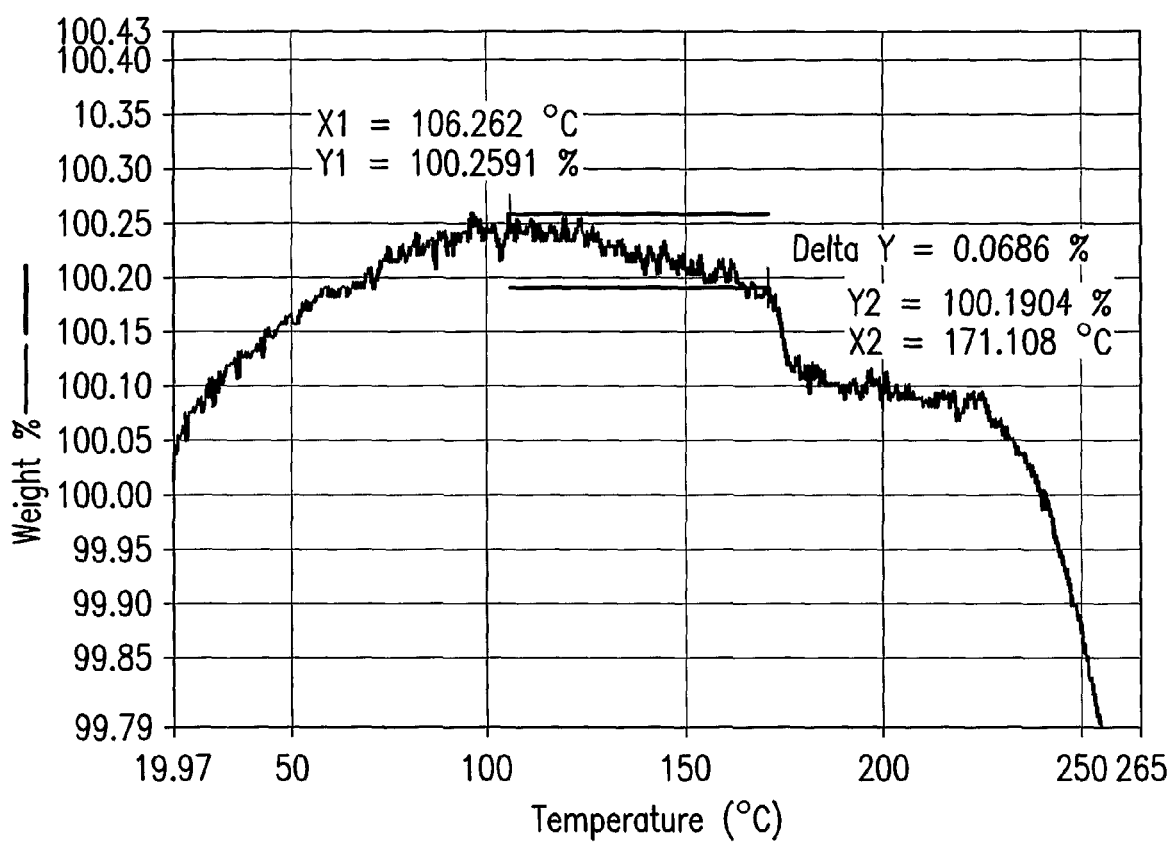
FIG. 16 provides a characteristic thermogravimetric analysis (TGA) curve of the Free Acid Form C of Compound II.

Free Acid Form C is crystalline as shown by XRPD pattern in FIG. 14. Free Acid Form C has a melting onset at 171.8° C., peak at 172.8° C. and a heat of melting of 107.2 J/g as shown in the DSC in FIG. 15. The TGA of Free Acid Form C shows a minimal weight loss of <0.1% as shown by the curve in FIG. 16. FIG. 14 shows a characteristic X-ray powder diffraction pattern of free acid crystalline Form C. Free acid crystalline Form C is characterized by peaks at 21.6°, 17° and 16.3° 2θ. Free acid crystalline Form C can be further characterized by peaks at 13.6°, 5.5° and 7.9° 2θ. Free acid crystalline Form C can be further characterized by peaks at 18.4°, 20.8° and 20.1° 2θ.

EXAMPLE 8

Form V Sodium Salt

Figure 17:
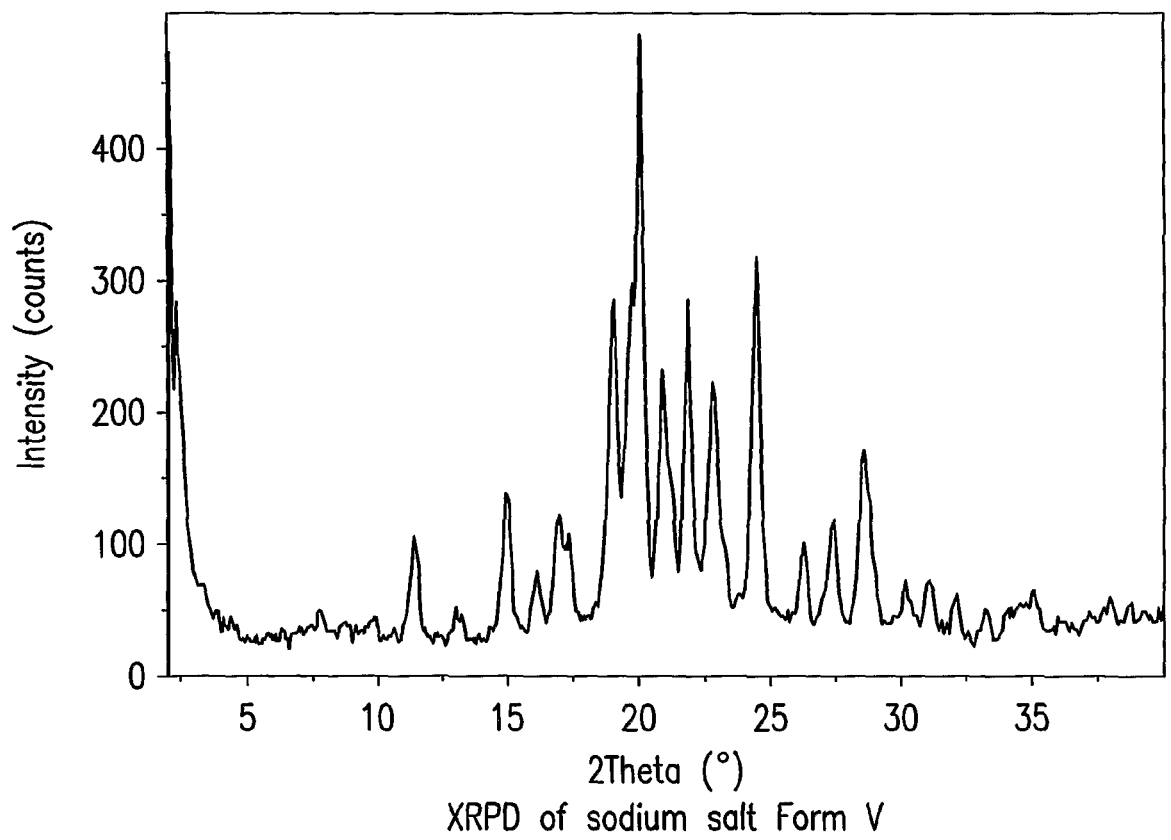
FIG. 17 provides a characteristic X-ray powder diffraction pattern of the Sodium Salt Form V of Compound II.
Figure 18:
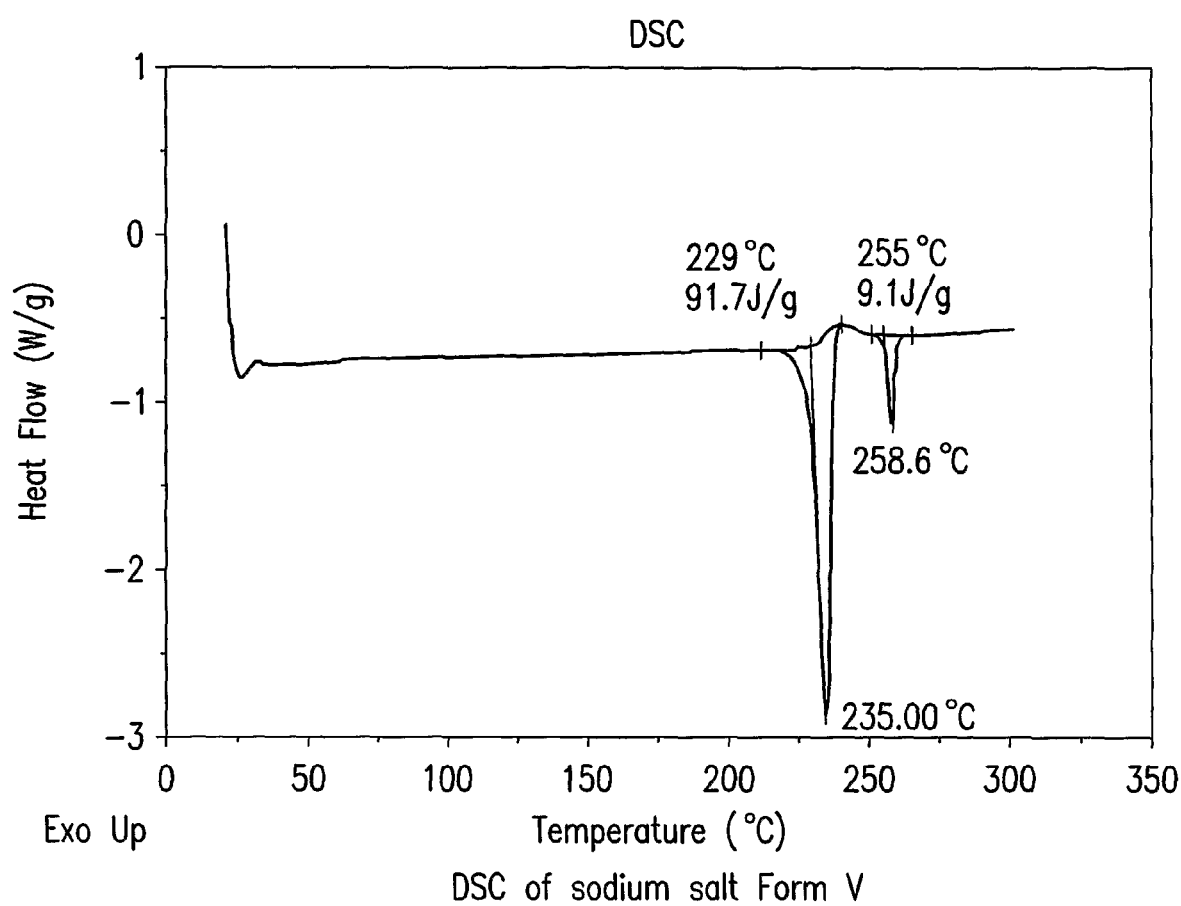
FIG. 18 provides a characteristic differential scanning calorimetry (DSC) curve of the Sodium Salt Form V of Compound II.
Figure 19:
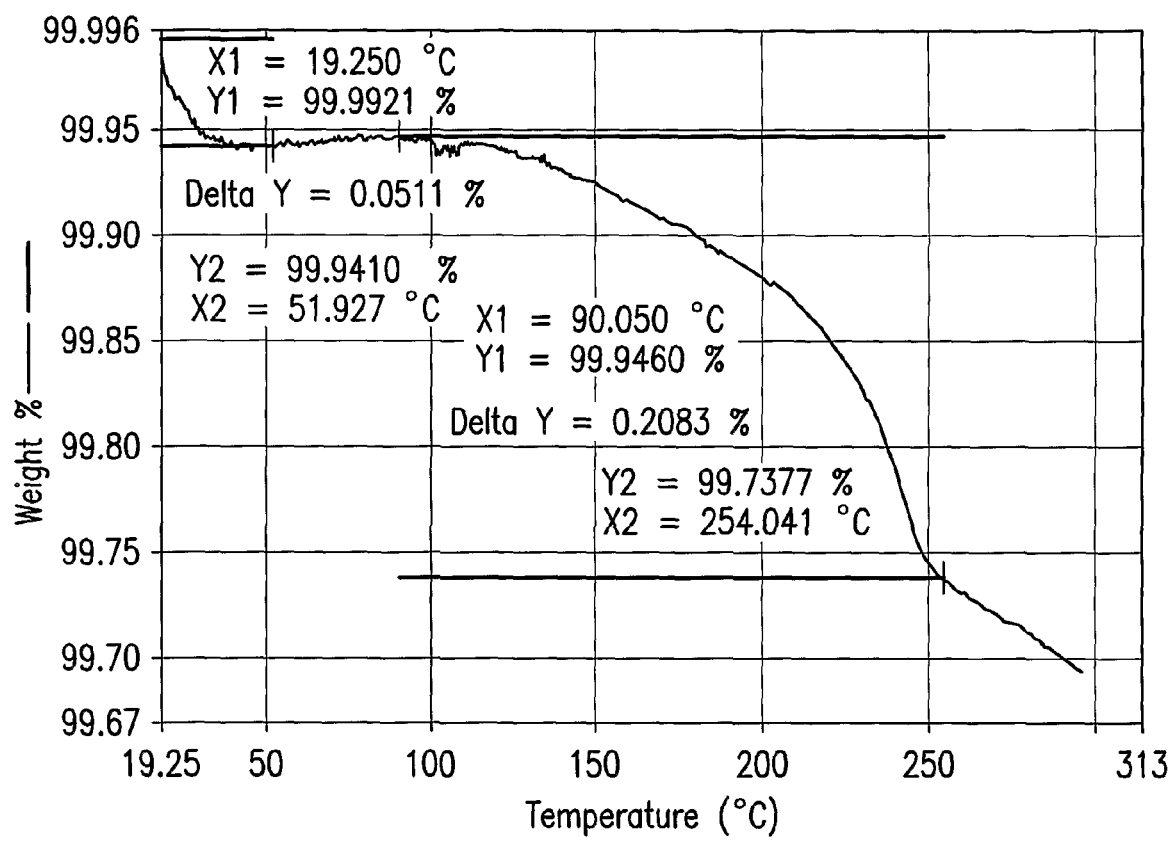
FIG. 19 provides a characteristic thermogravimetric analysis (TGA) curve of the Sodium Salt Form V of Compound II.

The sodium salt Form V was analyzed by XRPD, DSC and TG. It is crystalline (FIG. 17). The DSC shows a melting point onset of 229° C., peak at 235° C., and a second endotherm with onset at 255° C. and peak at 258.6° C. (FIG. 18). TGA (FIG. 19) shows minimal weight loss of 0.2% up to 254° C. FIG. 17 shows a characteristic X-ray powder diffraction pattern of crystalline sodium salt Form V. Crystalline sodium salt Form V is characterized by peaks at 20°, 19.7° and 24.4° 2θ. Crystalline sodium salt Form V can be further characterized by peaks at 19°, 21.8° and 20.9° 2θ. Crystalline sodium salt Form V can be further characterized by peaks at 11.4°, 15° and 16.1° 2θ.

Comparison of Crystal Forms

Figure 20:
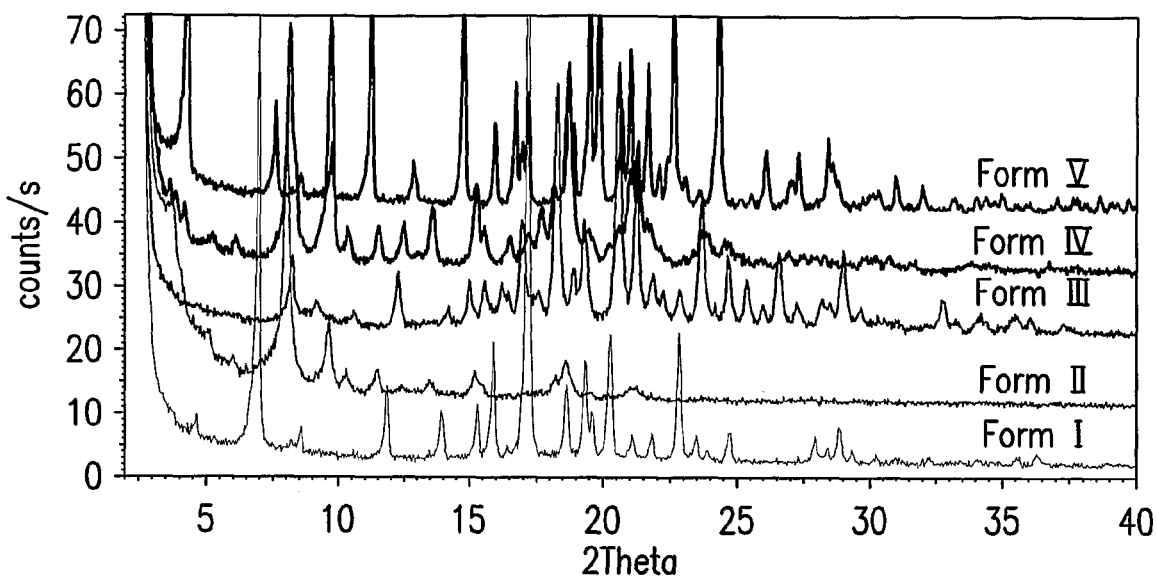
FIG. 20 provides X-ray powder diffraction patterns of all 5 crystal forms of the sodium salts of Compound II on the same scale, showing that they are different and distinct.

FIG. 20 shows the XRPD patterns of all five crystal forms (I, II, III, IV, and V) of the sodium salt of Compound II on the same scale.

Figure 21:
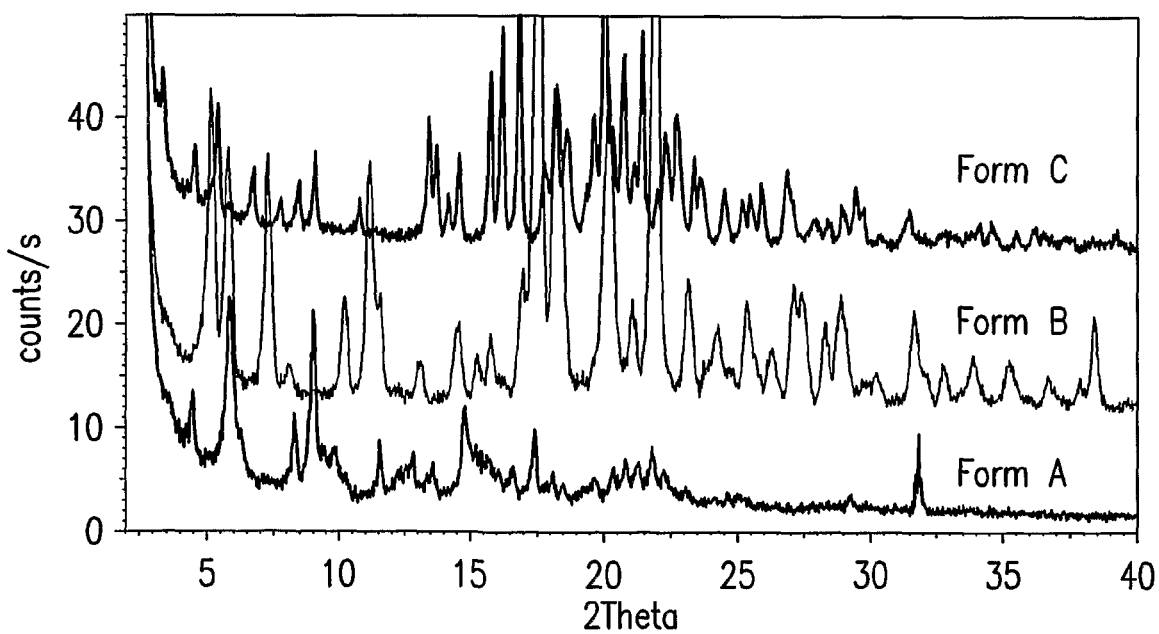
FIG. 21 provides X-ray powder diffraction patterns of all 3 crystal forms of the free acid of Compound II on the same scale, showing that they are different and distinct.

FIG. 21 shows the XRPD patterns of all three crystal forms (A, B, and C) of the free acid of Compound II on the same scale.

In both figures, it can be seen that the crystal forms of the sodium salt and the free acid of Compound II have unique XRPD patterns.

EXAMPLE 9

The conversion of Compound 4 of the synthetic procedure in Example 1 to Compound 6 can also be carried out by the following procedure:

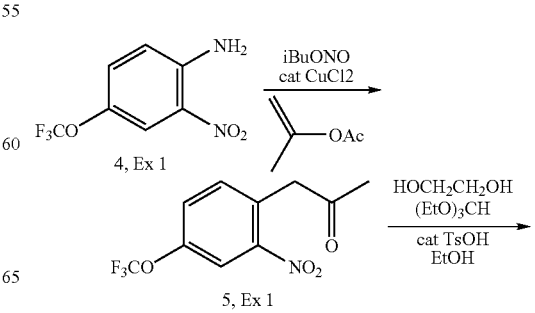

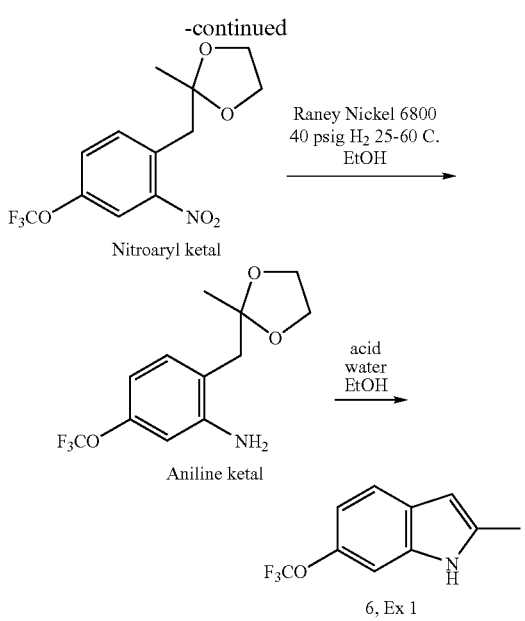

Meerwein Reaction and Ketalization. A solution of nitroaniline 4 (22.21 g) in isopropenyl acetate (22 mL) and a solution of iBuONO (94%, 13.71 g) are each added from separate addition funnels at ca the same rate (±10%) over 1 h to a suspension of CuCl2 (2.01 g) in 200 mL isopropenyl acetate maintained at 40-50° C. The mixture is aged for 1h at 40-50° C. and cooled to 25° C. Toluene (100 mL) is added and the mixture is washed with 1M HCl (2×15 mL); most of the copper is concentrated in these two small aq. washes) and then with water (2×100 mL). The organic phase is concentrated to 50 mL and at constant volume solvent switched to toluene using 100 mL toluene at 200 Torr. The mixture is then constant volume solvent switched to EtOH using 150 mL EtOH at 200 Torr. The solution containing nitroketone 5 in 50 mL EtOH was mixed with ethylene glycol (9.31 g), (EtO)$_3$CH (21.03 g), and p-TsOH (0.50 g), and the solution was heated to 45° C. for 16 h or 80° C. for 1-2 h and was then cooled to 25 C. Conversion of the nitroketone 5 was monitored by HPLC.

Hydrogenation. Triethylamine (0.28 g) was added to the solution of crude nitroaryl ketal from the previous step (the pH changes from <2 to >5 as measured using pH paper), and the resulting mixture was placed in a pressure bottle. Raney nickel (22.2 g of wet slurry) was added, and the mixture was hydrogenated at 40 psig and 25-70° C. (exothermic) for 2 h. The mixture was treated with Darco G60 (1.1 g) for 20 min at 25-40 C, and was then filtered through Solkafloc, washing the pad with EtOH (50 mL).

Hydrolysis/Cyclization. A solution of citric acid (27.3 g) in 25.9 mL of water was added to the solution of the crude product from the previous step. The mixture was aged 6 hours to achieve ~95% conversion at 80° C. The mixture was then cooled to 20° C. and was charged with 50% NaOH until a sufficient amount was added to bring pH to 5. The batch was concentrated to ~50 ml at 200 Torr, then the solvent was switched to toluene to remove ethanol from the distillates. The toluene solution was washed with water (2×50 mL). The solvent was then switched to water at atmospheric pressure. The desired indole product 6 is volatile and starts to come over in the distillates as the toluene is removed. The indole is insoluble in water and has a melting point of ~83° C. As the distillation continues, the vapors are either sparged into a toluene/water mixture to capture the indole in the toluene layer, or the vapors are condensed at ~85° C. to prevent solid indole (melting point ~83° C.) from blocking the condenser. The majority of the indole still remains in the distillation vessel after the toluene has been removed and continues to distill out with the water, so that a steam distillation (steam stripping) is carried out. Water is recycled from the distillates back to the distillation vessel until all of the indole has been collected in the toluene layer of the distillate receiver. Approximately 65 ml of water is distilled per grain of indole.

EXAMPLE OF A PHARMACEUTICAL COMPOSITION

The crystalline dihydrate form of Compound I may be formulated as follows. A 100 mg dosage form of Compound I is comprised of 107 mg of Compound I dihydrate in the form of granules that are made by roller compaction of the crystalline dihydrate with Avicel (filler), lactose (filler), croscarmellose sodium (disintegrant), sodium lauryl sulfate (surfactant), and magnesium stearate (lubricant). The granules are then filled into gelatin capsules or compacted into tablets. Preferably the tablets are coated with a dark opaque film.

A 100 mg dosage form of Compound II is made by formulating 100 mg of Form C crystals using the same procedure as described above.

What is claimed is:

1. A compound having the name (2R)-2-{3-[3-(4-methoxybenzoyl)-2-methyl-6-(trifluoromethoxy)-1H-indol-1-yl]phenoxy}butanoic acid, the structural formula I,

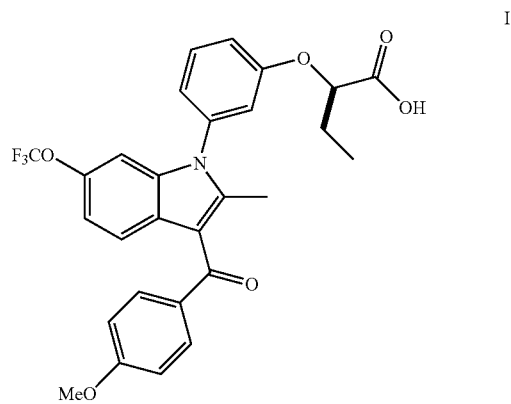

and characterized as being a crystalline free acid dehydrate, and further characterized as having at least one XRPD peak selected from the group consisting of: 16.8°, 19.6°, 5.7°, 22.4°, 7.7°, 15.2°, 24.6°, 11.2°, and 22.8° 2θ.

2. A pharmaceutical composition in the form of a tablet or capsule comprising a compound in accordance with claim 1 in combination with one or more pharmaceutically acceptable carriers or excipients.

3. A compound having the name (2R)-2-{3-[3-(4-methoxybenzoyl) -2-methyl-6-(trifluoromethoxy)-1H-indol-1-yl]phenoxy}butanoic acid, the structural formula I,

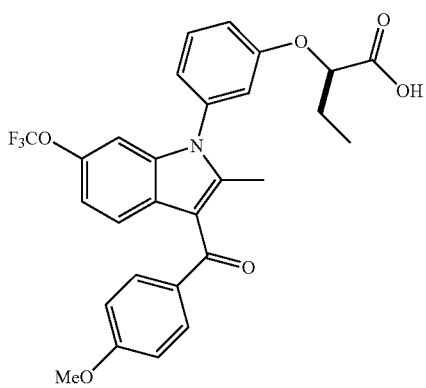

and characterized as being a crystalline free acid dehydrate, and further characterized as having at least one chemical shift value in the solid-state carbon-13 CPMAS NMR spectrum having chemical shift values selected from the group consisting of 11.1, 56.2, 190.7, 13.9, 78.3, 174.2, 164.1, and 157.6 ppm.

4. A pharmaceutical composition in the form of a tablet or capsule comprising a compound in accordance with claim 3 in combination with one or more pharmaceutically acceptable carriers or excipients.

* * * * *